United States Patent
Reynolds

(10) Patent No.: US 12,239,539 B2
(45) Date of Patent: Mar. 4, 2025

(54) JOINT REPLACEMENT PROSTHESIS WITH TRANS-CORTICAL STEMS

(71) Applicant: WRIGHT MEDICAL TECHNOLOGY, INC., Memphis, TN (US)

(72) Inventor: David G. Reynolds, Fairport, NY (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 166 days.

(21) Appl. No.: 17/824,061

(22) Filed: May 25, 2022

(65) Prior Publication Data

US 2022/0387178 A1    Dec. 8, 2022

Related U.S. Application Data

(60) Provisional application No. 63/197,557, filed on Jun. 7, 2021.

(51) Int. Cl.
*A61F 2/30* (2006.01)

(52) U.S. Cl.
CPC ............. *A61F 2/30734* (2013.01); *A61F 2002/30217* (2013.01); *A61F 2002/30329* (2013.01); *A61F 2002/30349* (2013.01); *A61F 2002/3035* (2013.01); *A61F 2002/30433* (2013.01); *A61F 2002/30507* (2013.01); *A61F 2002/30609* (2013.01); *A61F 2002/30787* (2013.01); *A61F 2002/30894* (2013.01)

(58) Field of Classification Search
CPC ............. A61F 2/30734; A61F 2002/30894
See application file for complete search history.

(56) References Cited

U.S. PATENT DOCUMENTS

| | | | |
|---|---|---|---|
| 3,839,742 | A | 10/1974 | Link |
| 3,872,519 | A | 3/1975 | Giannestras et al. |
| 3,886,599 | A | 6/1975 | Schlein |
| 3,889,300 | A | 6/1975 | Smith |
| 3,896,502 | A | 7/1975 | Lennox |
| 3,896,503 | A | 7/1975 | Freeman et al. |
| 3,975,778 | A | 8/1976 | Newton, III |
| 3,987,500 | A | 10/1976 | Schlein |
| 4,021,864 | A | 5/1977 | Waugh |

(Continued)

FOREIGN PATENT DOCUMENTS

| | | | |
|---|---|---|---|
| CA | 2836651 | | 3/2016 |
| EP | 0010527 | * | 4/1980 ............... A61F 2/32 |

(Continued)

OTHER PUBLICATIONS

Search report issued for European patent application No. 13198280 dated Feb. 5, 2014.

(Continued)

*Primary Examiner* — Melanie R Tyson
*Assistant Examiner* — Yasniary De La Caridad Morales
(74) *Attorney, Agent, or Firm* — DUANE MORRIS LLP

(57) ABSTRACT

Provided is a novel joint replacement prosthesis that includes a base component, and one or more modular stems. The base component includes a bone-facing surface including one or more stem connectors configured for receiving and forming connections with the one or more modular stems inserted from the bone-facing surface side.

18 Claims, 21 Drawing Sheets

(56) References Cited

U.S. PATENT DOCUMENTS

| | | | |
|---|---|---|---|
| 4,069,518 A | 1/1978 | Groth, Jr. et al. | |
| 4,156,944 A | 6/1979 | Schreiber et al. | |
| 4,166,292 A | 9/1979 | Bokros | |
| 4,204,284 A | 5/1980 | Koeneman | |
| 4,232,404 A | 11/1980 | Samuelson et al. | |
| 4,309,778 A | 1/1982 | Buechel et al. | |
| 4,470,158 A | 9/1984 | Pappas et al. | |
| 4,755,185 A | 7/1988 | Tarr | |
| 4,968,316 A | 11/1990 | Hergenroeder | |
| 5,041,139 A | 8/1991 | Brånemark | |
| 5,137,535 A * | 8/1992 | Keller | A61F 2/3609 623/20.36 |
| 5,312,412 A | 5/1994 | Whipple | |
| 5,326,365 A | 7/1994 | Alvine | |
| 5,354,300 A | 10/1994 | Goble et al. | |
| 5,423,825 A | 6/1995 | Levine | |
| 5,476,466 A | 12/1995 | Barrette et al. | |
| 5,593,449 A * | 1/1997 | Roberson, Jr. | A61F 2/30749 623/23.15 |
| 5,601,563 A | 2/1997 | Burke et al. | |
| 5,609,641 A | 3/1997 | Johnson et al. | |
| 5,628,749 A | 5/1997 | Vendrely et al. | |
| 5,634,927 A | 6/1997 | Houston et al. | |
| 5,667,511 A | 9/1997 | Vendrely et al. | |
| 5,674,223 A | 10/1997 | Cipolletti et al. | |
| 5,735,904 A | 4/1998 | Pappas | |
| 5,766,259 A | 6/1998 | Sammarco | |
| 5,776,200 A | 7/1998 | Johnson et al. | |
| 5,817,097 A | 10/1998 | Howard et al. | |
| 5,824,106 A | 10/1998 | Fournal | |
| 5,879,389 A | 3/1999 | Koshino | |
| 5,885,299 A | 3/1999 | Winslow et al. | |
| 5,888,203 A | 3/1999 | Goldberg | |
| 5,897,559 A | 4/1999 | Masini | |
| 5,935,132 A | 8/1999 | Bettuchi et al. | |
| 6,002,859 A | 12/1999 | DiGioia, III et al. | |
| 6,033,405 A | 3/2000 | Winslow et al. | |
| 6,102,952 A | 8/2000 | Koshino | |
| 6,183,519 B1 | 2/2001 | Bonnin et al. | |
| 6,245,109 B1 | 6/2001 | Mendes et al. | |
| 6,342,056 B1 | 1/2002 | Mac-Thiong et al. | |
| 6,344,043 B1 | 2/2002 | Pappas | |
| 6,409,767 B1 | 6/2002 | Pericé et al. | |
| 6,436,146 B1 | 8/2002 | Hassler et al. | |
| 6,478,800 B1 | 11/2002 | Fraser et al. | |
| 6,520,964 B2 | 2/2003 | Tallarida et al. | |
| 6,530,930 B1 | 3/2003 | Marino et al. | |
| 6,610,067 B2 | 8/2003 | Tallarida et al. | |
| 6,610,095 B1 | 8/2003 | Pope et al. | |
| 6,620,168 B1 | 9/2003 | Lombardo et al. | |
| 6,645,215 B1 | 11/2003 | McGovern et al. | |
| 6,663,669 B1 | 12/2003 | Reiley | |
| 6,673,116 B2 | 1/2004 | Reiley | |
| 6,679,917 B2 | 1/2004 | Ek | |
| 6,719,799 B1 | 4/2004 | Kropf | |
| 6,824,567 B2 | 11/2004 | Tornier et al. | |
| 6,852,130 B2 | 2/2005 | Keller et al. | |
| 6,860,902 B2 | 3/2005 | Reiley | |
| 6,863,691 B2 | 3/2005 | Short et al. | |
| 6,875,222 B2 | 4/2005 | Long et al. | |
| 6,875,236 B2 | 4/2005 | Reiley | |
| 6,926,739 B1 | 8/2005 | O'Connor et al. | |
| 6,939,380 B2 | 9/2005 | Guzman | |
| 6,942,670 B2 | 9/2005 | Heldreth et al. | |
| 7,001,394 B2 | 2/2006 | Gundlapalli et al. | |
| 7,011,687 B2 | 3/2006 | Deffenbaugh et al. | |
| 7,025,790 B2 | 4/2006 | Parks et al. | |
| 7,163,541 B2 | 1/2007 | Ek | |
| 7,238,190 B2 | 7/2007 | Schon et al. | |
| 7,252,684 B2 | 8/2007 | Dearnaley | |
| 7,314,488 B2 | 1/2008 | Reiley | |
| 7,323,012 B1 | 1/2008 | Stone et al. | |
| 7,476,227 B2 | 1/2009 | Tornier et al. | |
| 7,481,814 B1 | 1/2009 | Metzger | |
| 7,485,147 B2 | 2/2009 | Papps et al. | |
| 7,534,246 B2 | 5/2009 | Reiley et al. | |
| 7,534,270 B2 | 5/2009 | Ball | |
| 7,615,082 B2 | 11/2009 | Naegerl et al. | |
| 7,618,421 B2 | 11/2009 | Axelson, Jr. et al. | |
| 7,625,409 B2 | 12/2009 | Saltzman et al. | |
| 7,641,697 B2 | 1/2010 | Reiley | |
| 7,678,151 B2 | 3/2010 | Ek | |
| 7,713,305 B2 | 5/2010 | Ek | |
| 7,717,920 B2 | 5/2010 | Reiley | |
| 7,763,080 B2 | 7/2010 | Southworth | |
| 7,803,158 B2 | 9/2010 | Hayden | |
| 7,850,698 B2 | 12/2010 | Straszheim-Morley et al. | |
| 7,896,883 B2 | 3/2011 | Ek et al. | |
| 7,896,885 B2 | 3/2011 | Miniaci et al. | |
| 7,909,882 B2 | 3/2011 | Stinnette | |
| 7,963,996 B2 | 6/2011 | Saltzman et al. | |
| 8,002,841 B2 | 8/2011 | Hasselman | |
| 8,012,217 B2 | 9/2011 | Strzepa et al. | |
| 8,034,114 B2 | 10/2011 | Reiley | |
| 8,034,115 B2 | 10/2011 | Reiley | |
| 8,048,164 B2 | 11/2011 | Reiley | |
| 8,110,006 B2 | 2/2012 | Reiley | |
| 8,114,091 B2 | 2/2012 | Ratron et al. | |
| 8,167,888 B2 | 5/2012 | Steffensmeier | |
| 8,172,850 B2 | 5/2012 | McMinn | |
| 8,177,841 B2 | 5/2012 | Ek | |
| 8,268,007 B2 | 9/2012 | Barsoum et al. | |
| 8,303,667 B2 | 11/2012 | Younger | |
| 8,313,492 B2 | 11/2012 | Wong et al. | |
| 8,317,797 B2 | 11/2012 | Rasmussen | |
| 8,323,346 B2 | 12/2012 | Tepic | |
| 8,337,503 B2 | 12/2012 | Lian | |
| 8,361,159 B2 | 1/2013 | Ek | |
| 8,475,463 B2 | 7/2013 | Lian | |
| 8,491,596 B2 | 7/2013 | Long et al. | |
| 8,808,303 B2 | 8/2014 | Stemniski et al. | |
| 8,911,444 B2 | 12/2014 | Bailey | |
| 9,492,281 B2 | 11/2016 | Rouyer et al. | |
| 9,907,561 B2 | 3/2018 | Luna et al. | |
| 10,034,678 B2 | 7/2018 | Park et al. | |
| 10,039,558 B2 | 8/2018 | Park et al. | |
| 10,206,688 B2 | 2/2019 | Park et al. | |
| 2002/0068977 A1 | 6/2002 | Jackson | |
| 2002/0082607 A1 | 6/2002 | Heldreth et al. | |
| 2002/0133164 A1 | 9/2002 | Williamson | |
| 2002/0173853 A1 | 11/2002 | Corl, III et al. | |
| 2003/0208280 A1 | 11/2003 | Tohidi | |
| 2003/0236522 A1 | 12/2003 | Long et al. | |
| 2004/0030399 A1 | 2/2004 | Asencio | |
| 2004/0039394 A1 | 2/2004 | Conti et al. | |
| 2004/0068322 A1 | 4/2004 | Ferree | |
| 2004/0167631 A1 | 8/2004 | Luchesi et al. | |
| 2004/0186585 A1 | 9/2004 | Feiwell | |
| 2004/0216259 A1 | 11/2004 | Ponziani | |
| 2004/0236431 A1 | 11/2004 | Sekel | |
| 2005/0004676 A1 | 1/2005 | Schon et al. | |
| 2005/0165408 A1 | 7/2005 | Puno et al. | |
| 2005/0192674 A1 | 9/2005 | Ferree | |
| 2006/0009857 A1 | 1/2006 | Gibbs et al. | |
| 2006/0020345 A1 | 1/2006 | O'Connor et al. | |
| 2006/0036257 A1 | 2/2006 | Steffensmeier | |
| 2006/0116679 A1 | 6/2006 | Lutz et al. | |
| 2006/0142870 A1 | 6/2006 | Robinson et al. | |
| 2006/0229730 A1 * | 10/2006 | Railey | A61B 17/15 623/23.44 |
| 2006/0235541 A1 | 10/2006 | Hodorek | |
| 2006/0247788 A1 | 11/2006 | Ross | |
| 2007/0038303 A1 | 2/2007 | Myerson et al. | |
| 2007/0100346 A1 | 5/2007 | Wyss et al. | |
| 2007/0112431 A1 | 5/2007 | Kofoed | |
| 2007/0129808 A1 * | 6/2007 | Justin | A61F 2/389 623/22.36 |
| 2007/0162025 A1 | 7/2007 | Tornier et al. | |
| 2007/0173944 A1 | 7/2007 | Keller et al. | |
| 2007/0173947 A1 | 7/2007 | Ratron | |
| 2007/0213830 A1 | 9/2007 | Ammann et al. | |
| 2007/0233129 A1 | 10/2007 | Bertagnoli et al. | |
| 2007/0276400 A1 | 11/2007 | Moore et al. | |
| 2007/0288030 A1 | 12/2007 | Metzger et al. | |

(56) References Cited

U.S. PATENT DOCUMENTS

| | | |
|---|---|---|
| 2008/0015602 A1 | 1/2008 | Axelson |
| 2008/0097617 A1 | 4/2008 | Fellinger et al. |
| 2008/0103603 A1 | 5/2008 | Hintermann |
| 2008/0109081 A1 | 5/2008 | Bao et al. |
| 2008/0195233 A1 | 8/2008 | Ferrari et al. |
| 2008/0215156 A1 | 9/2008 | Duggal et al. |
| 2008/0287954 A1 | 11/2008 | Kunz et al. |
| 2008/0312745 A1 | 12/2008 | Keller et al. |
| 2009/0024131 A1 | 1/2009 | Metzger et al. |
| 2009/0043310 A1 | 2/2009 | Rasmussen |
| 2009/0054992 A1 | 2/2009 | Landes et al. |
| 2009/0082875 A1 | 3/2009 | Long |
| 2009/0105767 A1 | 4/2009 | Reiley |
| 2009/0105840 A1 | 4/2009 | Reiley |
| 2009/0182433 A1 | 7/2009 | Reiley et al. |
| 2009/0198341 A1 | 8/2009 | Choi et al. |
| 2009/0234360 A1 | 9/2009 | Alexander |
| 2009/0276052 A1 | 11/2009 | Regala et al. |
| 2010/0010493 A1 | 1/2010 | Dower |
| 2010/0023066 A1 | 1/2010 | Long et al. |
| 2010/0023126 A1 | 1/2010 | Grotz |
| 2010/0057216 A1 | 3/2010 | Gannoe et al. |
| 2010/0069910 A1 | 3/2010 | Hasselman |
| 2010/0198355 A1 | 8/2010 | Kofoed et al. |
| 2010/0241237 A1 | 9/2010 | Pappas |
| 2010/0305572 A1 | 12/2010 | Saltzman et al. |
| 2010/0318088 A1 | 12/2010 | Warne et al. |
| 2010/0331984 A1 | 12/2010 | Barsoum et al. |
| 2011/0029090 A1 | 2/2011 | Zannis et al. |
| 2011/0035018 A1 | 2/2011 | Deffenbaugh et al. |
| 2011/0035019 A1 | 2/2011 | Goswami et al. |
| 2011/0106268 A1 | 5/2011 | Deffenbaugh et al. |
| 2011/0125200 A1 | 5/2011 | Hanson et al. |
| 2011/0125275 A1 | 5/2011 | Lipman et al. |
| 2011/0125284 A1 | 5/2011 | Gabbrielli et al. |
| 2011/0152868 A1 | 6/2011 | Kourtis et al. |
| 2011/0152869 A1 | 6/2011 | Ek et al. |
| 2011/0166608 A1 | 7/2011 | Duggal et al. |
| 2011/0190829 A1 | 8/2011 | Duggal et al. |
| 2011/0218542 A1 | 9/2011 | Lian |
| 2011/0218648 A1* | 9/2011 | Younger .................. A61F 2/64 623/47 |
| 2011/0253151 A1 | 10/2011 | Tochigi et al. |
| 2011/0276052 A1 | 11/2011 | Hasselman |
| 2011/0295380 A1 | 12/2011 | Long |
| 2012/0010718 A1 | 1/2012 | Still |
| 2012/0046753 A1 | 2/2012 | Cook et al. |
| 2012/0053644 A1 | 3/2012 | Landry et al. |
| 2012/0083789 A1 | 4/2012 | Blakemore et al. |
| 2012/0109131 A1 | 5/2012 | Vasarhelyi et al. |
| 2012/0109326 A1 | 5/2012 | Perler |
| 2012/0130376 A1 | 5/2012 | Loring et al. |
| 2012/0136443 A1 | 5/2012 | Wenzel |
| 2012/0185057 A1 | 7/2012 | Abidi et al. |
| 2012/0191210 A1 | 7/2012 | Ratron et al. |
| 2012/0239045 A1 | 9/2012 | Li |
| 2012/0245701 A1 | 9/2012 | Zak et al. |
| 2012/0271430 A1 | 10/2012 | Arnett et al. |
| 2012/0277745 A1 | 11/2012 | Lizee |
| 2013/0041473 A1 | 2/2013 | Rouyer et al. |
| 2013/0116797 A1 | 5/2013 | Coulange et al. |
| 2013/0190881 A1 | 7/2013 | Winslow et al. |
| 2016/0135815 A1 | 5/2016 | Loring et al. |
| 2018/0064537 A1* | 3/2018 | Pressacco ........... A61F 2/30749 |
| 2019/0038426 A1* | 2/2019 | Ek ....................... A61F 2/4202 |
| 2020/0352580 A1* | 11/2020 | Saltzman ........... A61B 17/1775 |

FOREIGN PATENT DOCUMENTS

| | | |
|---|---|---|
| EP | 2967697 | 4/2018 |
| EP | 3354233 | 10/2019 |
| GB | 2480846 | 12/2011 |
| JP | H11-500035 | 1/1999 |
| JP | 2006150055 | 6/2006 |
| JP | 2007518453 | 7/2007 |
| JP | 2007519477 | 7/2007 |
| JP | 2007536011 | 12/2007 |
| JP | 2011526189 | 10/2011 |
| JP | 2012518517 | 8/2012 |
| JP | 2013500810 | 1/2013 |
| JP | 2013511358 | 4/2013 |
| JP | 2014131738 | 7/2014 |
| WO | WO 9625106 | 8/1996 |
| WO | WO 0166021 A1 | 9/2001 |
| WO | WO 2005011523 A2 | 2/2005 |
| WO | WO 2006022923 | 3/2006 |
| WO | WO 2006023824 | 3/2006 |
| WO | WO 2006099270 | 9/2006 |
| WO | WO 2007084846 | 7/2007 |
| WO | WO 2009158522 | 12/2009 |
| WO | WO 2010099142 | 9/2010 |
| WO | WO 2011015863 | 2/2011 |
| WO | WO 2011063281 | 5/2011 |
| WO | WO 2011151657 | 12/2011 |
| WO | WO 2012088036 | 6/2012 |
| WO | WO 2012116089 | 8/2012 |

OTHER PUBLICATIONS

International Search Report for International patent application No. PCT/US2014/027448 dated Jul. 7, 2014.

International Preliminary Report on Patentability issued for International patent application No. PCT/US2014/027448, Sep. 15, 2015, 8 pages.

Partial European Search Report issued in connection with European patent application No. 14768333.8, Oct. 26, 2016, 6 pages.

Patent Examination Report No. 1 issued in connection with Australian patent application No. 2015202080, Jul. 5, 2016, 4 pages.

First Office Action issued for Japanese patent application No. 2016-117842, Sep. 12, 2017, 5 pages.

First Office Action issued in connection with corresponding Japanese Patent Application No. 2020-016447, Apr. 6, 2021, 4 pages.

Office Action in corresponding Canadian Patent Application No. 2,904,652, Jun. 2, 2020, 6 pages.

First Examination Report issued in corresponding Australian Patent Application No. 2019213412, Sep. 3, 2020, 5 pages.

First Office Action in corresponding Canadian Patent Application No. 2,904,652, Jan. 28, 2020, 5 pages.

Final Office Action issued in connection with corresponding Japanese Patent Application No. 206-502443, May 15, 2018, 3 pages.

Extended European Search Report issued in connection with corresponding European Patent Application No. 18160378.8, Jun. 29, 2018, 7 pages.

Second Office Action issued in connection with corresponding Chinese Patent Application No. 2018071101785100, dated Jul. 16, 2016, 6 pages.

First Office Action in corresponding Japanese Patent Application No. 2018-178853, Sep. 3, 2018, 3 pages.

Examination Report No. 1 issued in connection with corresponding Australian Patent Application No. 20182000073, Dec. 24, 2018, 3 pages.

First Office Action issued in connection with corresponding Japanese Patent Application No. 2018-092289, Mar. 5, 2019, 2 pages.

Extended European Search Report and Opinion in connection with European Patent Application No. 14768333.8, dated Jan. 30, 2017, 10 pages. *cited in parent.

Examination Report issued in connection with corresponding European Patent Application No. 22176302.2, Sep. 27, 2024, 8 pages.

* cited by examiner

JOINT REPLACEMENT PROSTHESIS WITH TRANS-CORTICAL STEMS

CROSS-REFERENCE TO RELATED APPLICATION

This application claims priority under 35 U.S.C. § 119(e) to U.S. Provisional Application No. 63/197,557, filed Jun. 7, 2021, the entirety of which is incorporated by reference herein.

FIELD

This disclosure relates generally to medical devices, and specifically to bone implants.

BACKGROUND

Joint replacement procedures often require obtaining rigid fixation of an implant component at the prepared end of a long bone, i.e. the metaphysis portion. For example, in some total joint replacement procedures, such as total ankle replacement can require obtaining rigid fixation of a stem portion of an implant into the distal end of a tibia. Stems are used in multiple implant designs such as, hip, knee, shoulder, ankle, for the robust stability they provide. In many existing joint replacement prosthesis systems, inserting a stem into an end of a long bone without significant violation of adjacent anatomy can be challenging.

In some prior-generation tibial implants, the anterior tibia cortex is removed to put a tibia stem in the tibia canal, then replace the anterior cortex in the hope that it will heal and attach to the remaining tibia bone and implant. This takes time, when successful, and does not always heal properly. Another prior-generation implant requires use of a drill up through the bottom of the foot and ream the tibia canal, and to assemble and implant a modular tibia stem. This requires an incision in the bottom of the foot, and a drilling procedure which could violate sensitive anatomy under the calcaneus (e.g., tendons, nerves, and blood vessels) as well and bone and potentially articular cartilage of the subtalar joint.

Thus, an improved joint replacement prosthesis is desired that enable inserting stem or stems in a metaphysis portion of a long bone in an approach that protects those sensitive regions, while still providing robust stabilization of the implant in the bone.

SUMMARY

According to one aspect, a novel joint replacement prosthesis is disclosed. The joint replacement prosthesis includes a base component, and one or more modular stems. The base component can comprise a bone-facing surface that includes one or more stem connectors configured to receive and form connections with the one or more modular stems inserted from the bone-facing surface side.

In some embodiments, a base component for a joint replacement prosthesis comprises: a bone-facing surface comprising one or more stem connectors, wherein each stem connector is configured to receive and form a connection with a modular stem inserted from the bone-facing surface side.

Also provided is a method for implanting a base component for a joint replacement prosthesis onto an end of a long bone, wherein the base component comprises: a bone-facing surface including one or more stem connectors configured to receive and form connections with one or more modular stems inserted from the bone-facing surface side, wherein each of the stem connectors defines a longitudinal axis, the method comprising: preparing the end of the long bone in a joint to receive the base component; drilling one or more holes into the long bone from a side, wherein each hole is oriented so that the hole is coaxial with the longitudinal axis of one of the one or more stem connectors; inserting a modular stem into one of the one or more holes to engage with one of the one or more stem connectors in the base component; and axially compressing the modular stem and said one of the one or more stem connectors together to form a connection between the modular stem and the stem connector.

BRIEF DESCRIPTION OF THE DRAWINGS

The description of the exemplary embodiments disclosed herein are intended to be read in connection with the accompanying drawings, which are to be considered part of the entire written description. All drawing figures are schematic illustrations and are not intended to show actual dimensions or proportions.

DETAILED DESCRIPTION

Figure 1A:
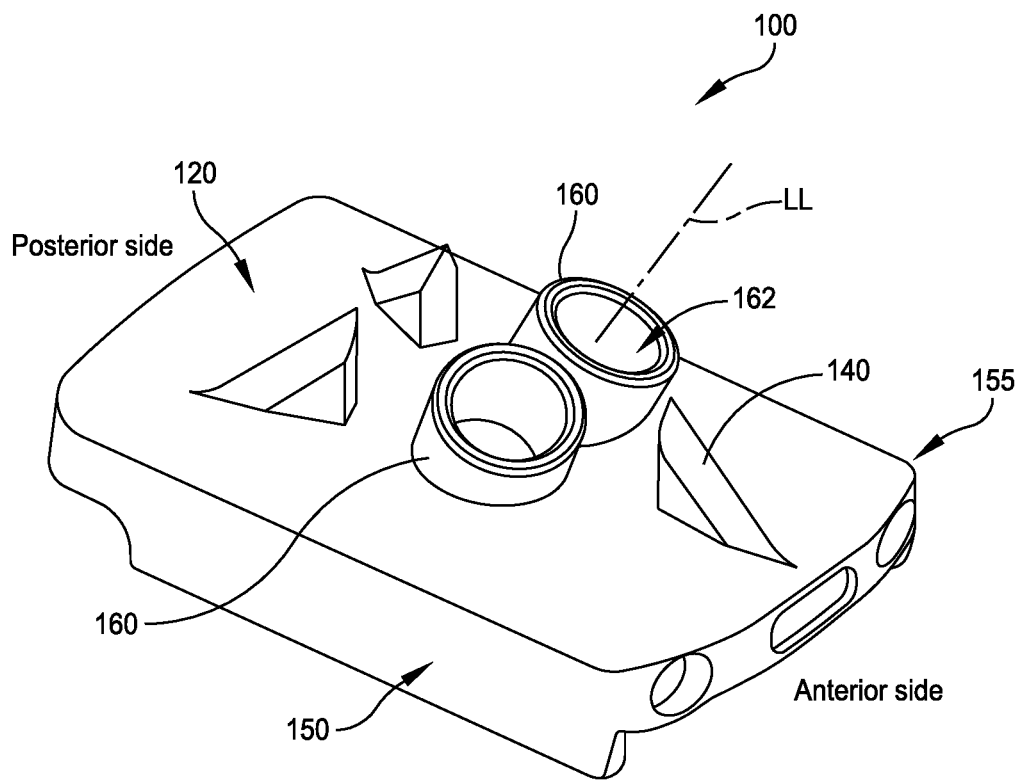
FIGS. 1A-1D are illustrations of a base component of a joint replacement prosthesis according to an embodiment.
Figure 1B:
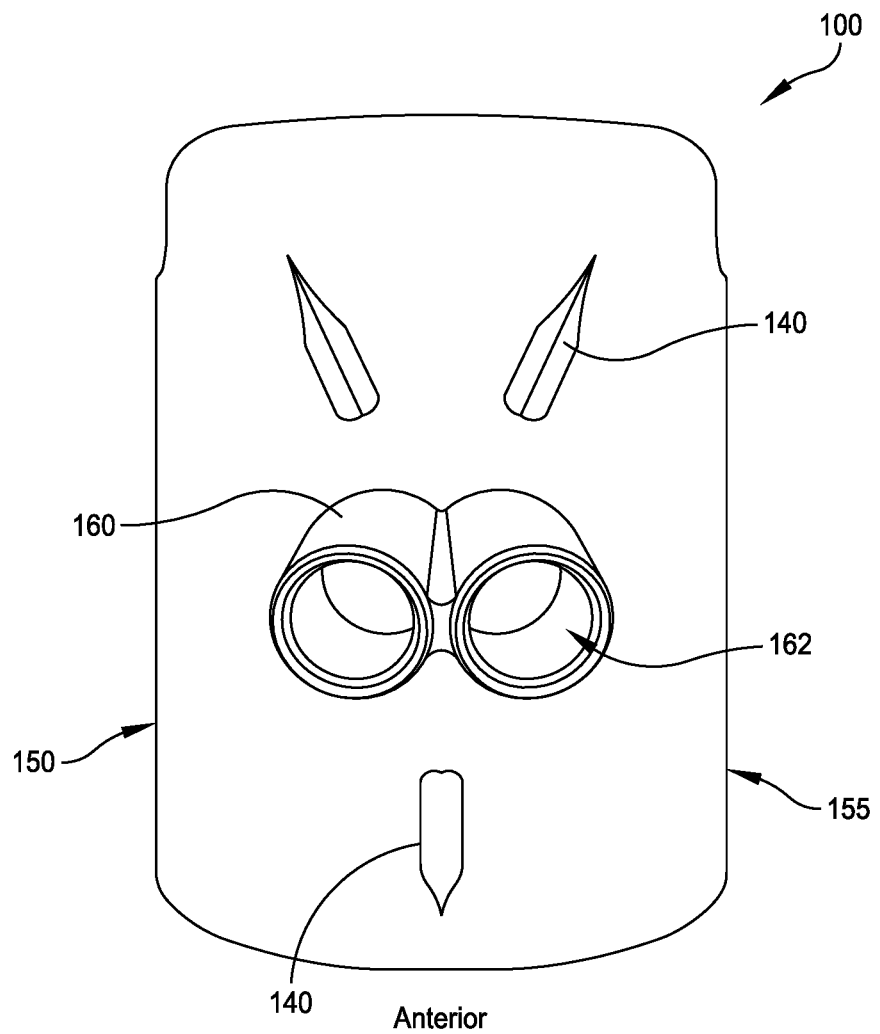

This description of the exemplary embodiments is intended to be read in connection with the accompanying drawings, which are to be considered part of the entire written description. The drawing figures are not necessarily to scale, and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The structures of the joint replacement prosthesis of the present disclosure will now be described using an example embodiment that is configured as a tibia baseplate in an ankle replacement whose stem(s) can be inserted into the prepared distal end of a tibia. However, the structures of the joint replacement prosthesis described herein can be implemented in other joint replacement applications as well. For example, as a tibia baseplate in knee joint replacement, a glenoid baseplate in a shoulder joint replacement, and for fixation of a talar implant.

The distal end of a tibia can be prepared in a similar manner as done in connection with existing tibia implant portion of total ankle replacement systems and the tibia canal can be prepared for the modular stem from the proximal direction without having to go through the patient's foot. The tibia base of the present disclosure can also comprise other beneficial features that enhance the stability of the tibia base in the tibia; including but not limited to fins, keels, ridges, posts, roughened surfaces, tapers, threads, screws, and expanding structures.

Referring to FIGS. 1A-3C, the present disclosure provides an example embodiment of a joint replacement prosthesis 10 that utilizes a base component 100 and one or more modular stems 200 that engages the base component 100. FIG. 1A is an illustration of an example of the base component 100 according to an embodiment. The base component 100 comprises a bone-facing surface 120 on which are provided one or more stem connectors 160 configured to receive and form connections with the one or more modular tibia stems 200 inserted from the bone-facing surface side. The base component 100 also includes side surfaces 150 and 155.

Figure 1C:
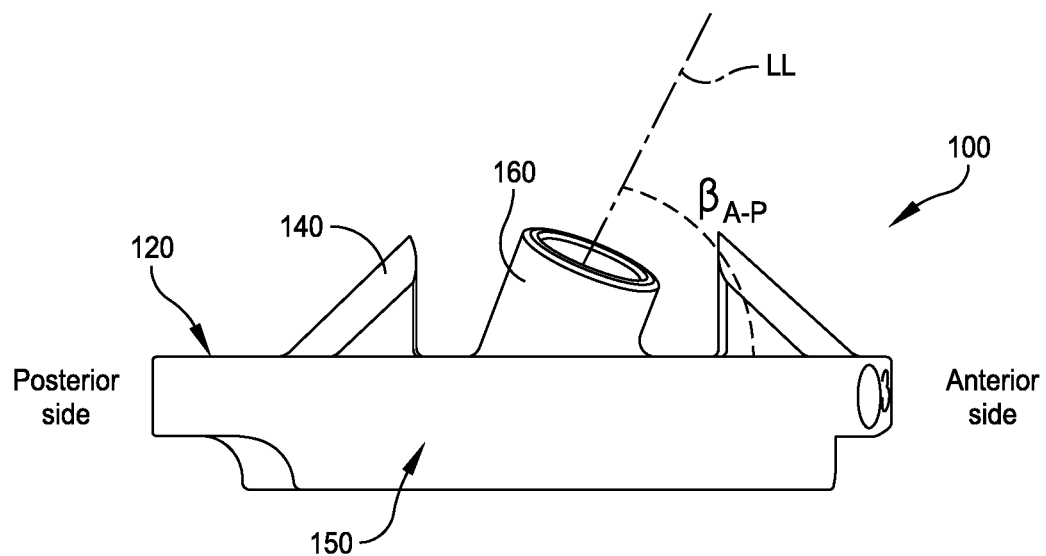
Figure 1D:
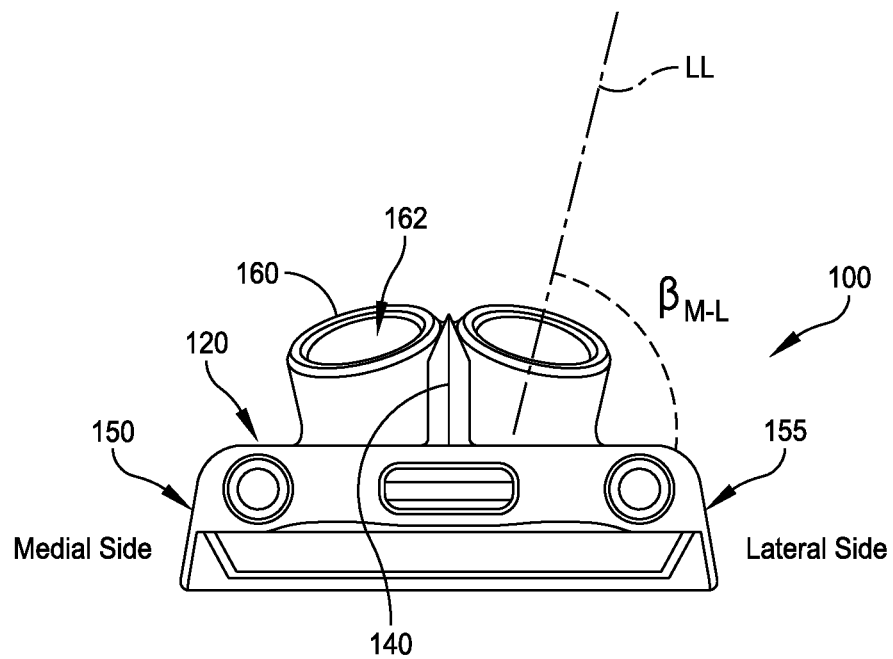
Figure 1E:
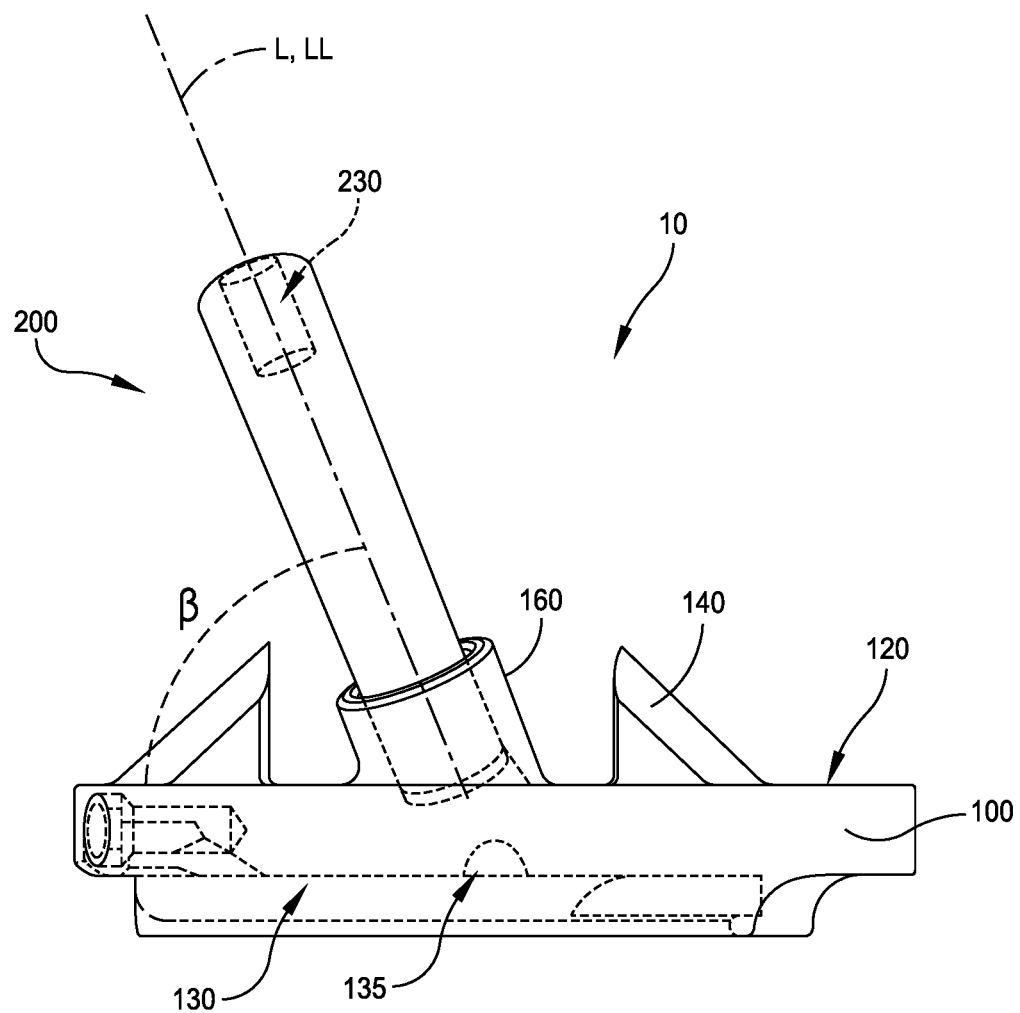
FIGS. 1E-1I are illustrations of the base component of FIGS. 1A-1D engaged with modular stems according to some embodiments.
Figure 1F:
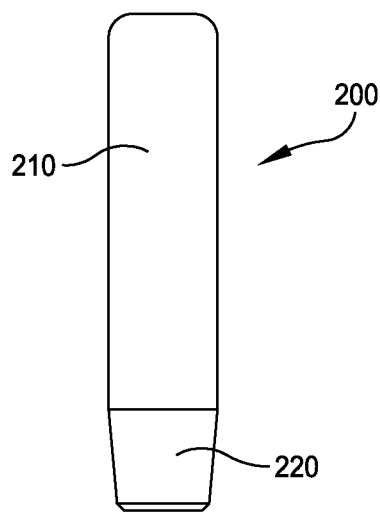

Referring to FIG. 1F, in some embodiments, each of the one or more modular stems 200 comprises a shaft portion 210 and a connecting portion 220. The connecting portion forms the connection with one of the stem connectors 160.

In some embodiments, the connecting portion 220 of the modular stems 200 can be configured with a male-type tapered surface, and each of the stem connectors 160 is configured as a recess having a female-type tapered sidewall surface that forms a friction lock connection with the connecting portion 220. As shown, the stem connector 160 comprises a blind hole 162 that has a complementary tapered sidewall surface forming the female-type tapered sidewall surface that engage with the male-type tapered surface of the connecting portion 220.

In some embodiments, the assignment of the male-type tapered surfaces and the female-type tapered surfaces can be reversed. For example, each of the stem connectors 160 can be configured as a post with a male-type tapered surface, and the connecting portion 220 of each of the one or more modular stems 200 can be configured as a recess having a female-type tapered sidewall surface that form the friction lock connection with one of the stem connectors 160.

In some embodiments, the male-type tapered surfaces and the female-type tapered surfaces referenced herein are configured as Morse taper surfaces forming the friction lock connections. Friction lock connections have proven to be highly reliable, and that the two locking surfaces can be configured to form a very tight joint with typically smaller than 1 micron gap. Compared to connection systems that are joined by screws, tapered friction lock connections are more robust in withstanding stress and can better prevent loosening.

Figure 5A:
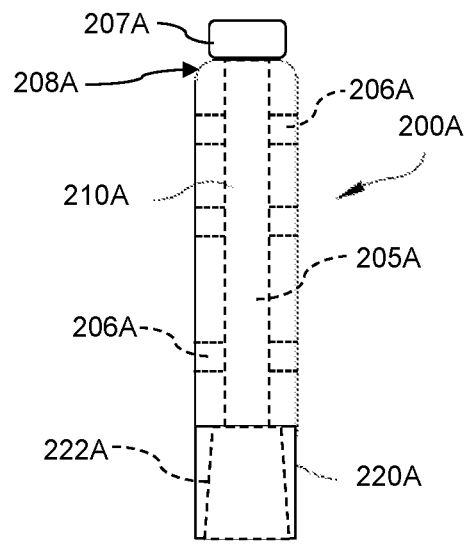
FIG. 5A is an illustration of another embodiment of a base component.
Figure 5C:
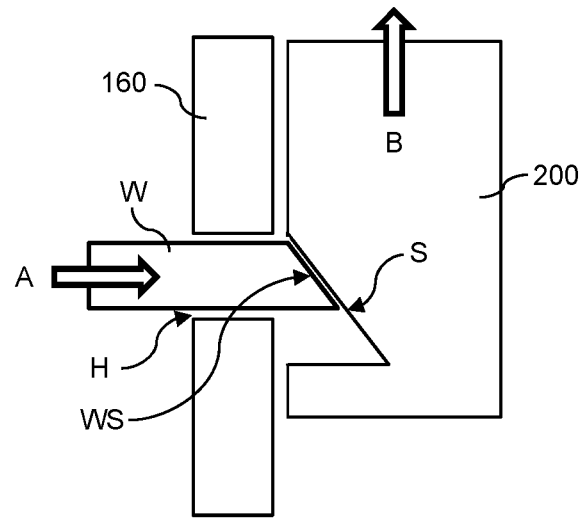
FIG. 5C us an illustration of a close up view of the exemplary structures for disconnecting two friction locked components such as a modular stem and a stem connector.
Figure 5B:
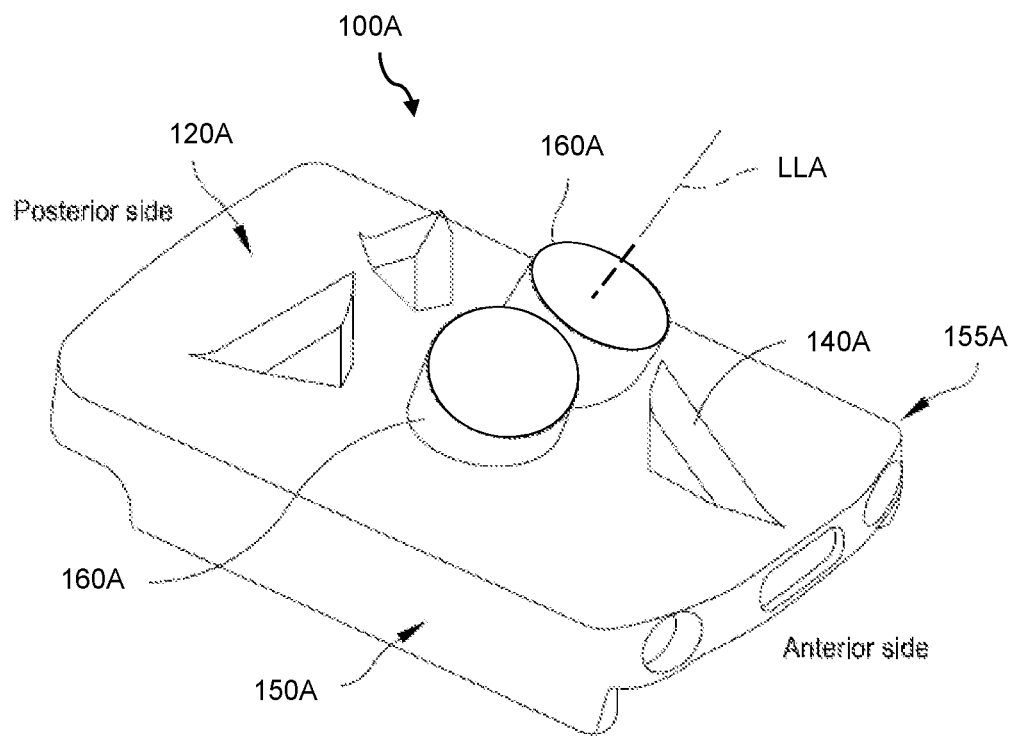
FIG. 5B is an illustration of another embodiment of a modular stem.

In the embodiments where the connecting portion 220 and the stem connector 160 form friction lock connections via cooperation of the above-mentioned tapered surfaces, for purposes of later revision or removal, the female-type tapered sidewall surface can be configured with one or more holes and the male-type tapered surface can be configured with a ramp-like structure for each of the one or more holes that are configured to enable disconnecting the friction lock connection. FIG. 5C shows a schematic example of a close up view of such structures. As an example, the annular sidewall of an embodiment of the stem connector 160 that has the female-type tapered surface that is connected to a male-type tapered surface of a stem 200 is shown. A hole H provided on the annular sidewall of the stem connector 160 is illustrated. The ramp-like structure provided on the stem 200 comprises a slanted surface S. When the friction lock connection is formed, each of the ramp-like structure would be aligned with each of the one or more holes in the female-type tapered sidewall. FIG. 5C shows a schematic close up view of the ramp-like structure aligned with the hole H provided on the annular sidewall of the stem connector 160. The slanted surface S of the ramp-like structure is oriented such that when a wedge W is driven into the hole H in the direction of the arrow A, the slanted surface WS of the wedge W operates on the slanted surface S of the ramp and pushes the stem 200 in the direction of the arrow B. This cooperation of the wedge W and the slanted surface S of the ramp-like structure pushes the two friction locked structures 160 and 200 apart and disconnect the friction lock connection.

In some embodiments, the connecting portion 220 has a diameter not greater than the diameter of the shaft portion 210. As will be discussed below in connection with FIGS. 2G-2I, because the modular stem 200 is inserted through a hole H drilled into a long bone, with the connecting portion 220 leading, to reach the receiving stem connector 160 in the base component 100 that is attached to the terminal end (can be proximal end or a distal end depending on the particular long bone of a joint involved) of the long bone, limiting the diameter of the connecting portion 220 to be not greater than the diameter of the shaft portion 210, allows the hole H drilled into the long bone to be kept substantially the same size as the diameter of the shaft portion 210 of the stem 200. This produces minimum space between the shaft portion 210 and the sidewall of the hole H so that once the stem 200 is situated inside the hole H, the stem 200 is snuggly fit within the long bone. This snug fit would be beneficial for securely joining the base component 100 to the long bone. The arrow D in FIG. 2I shows the inserting direction of the modular stem 200 in the hole H in the long bone.

In some embodiments, the diameter of the shaft portion 210 can vary throughout its length if desired. In some embodiments, the shaft portion 210 can have a constant diameter.

Figure 1G:
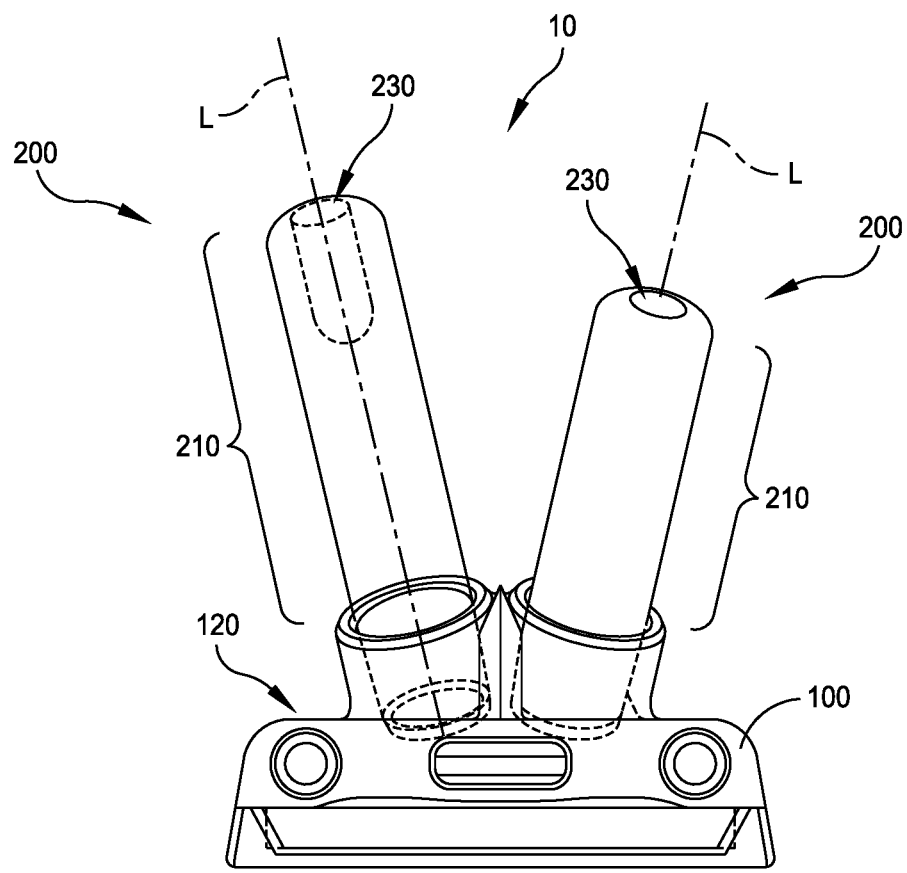
Figure 1H:
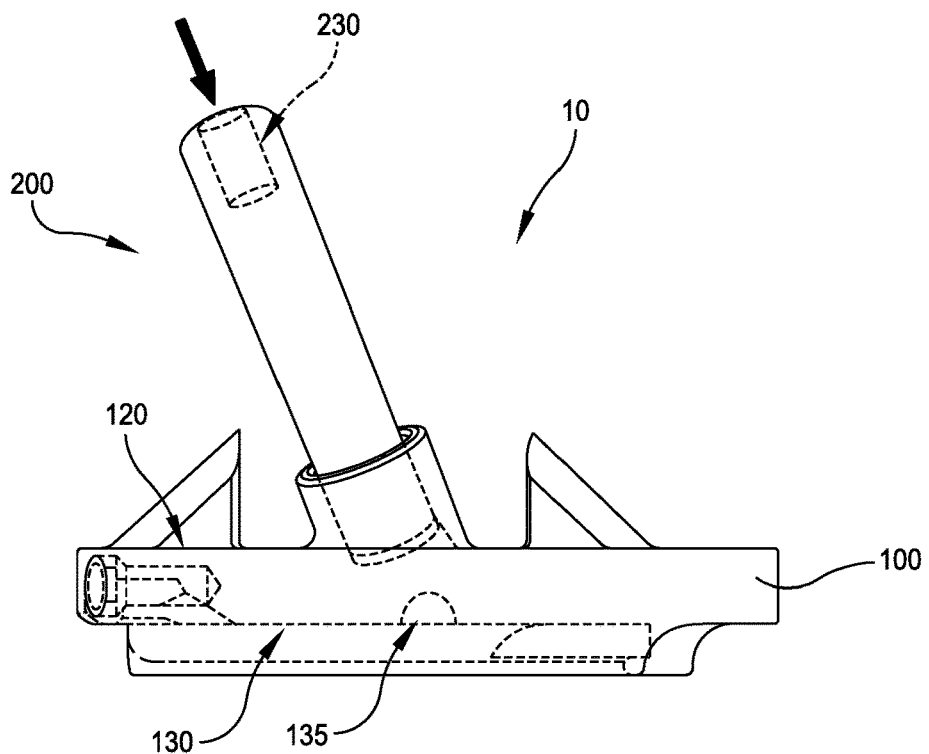
Figure 1I:
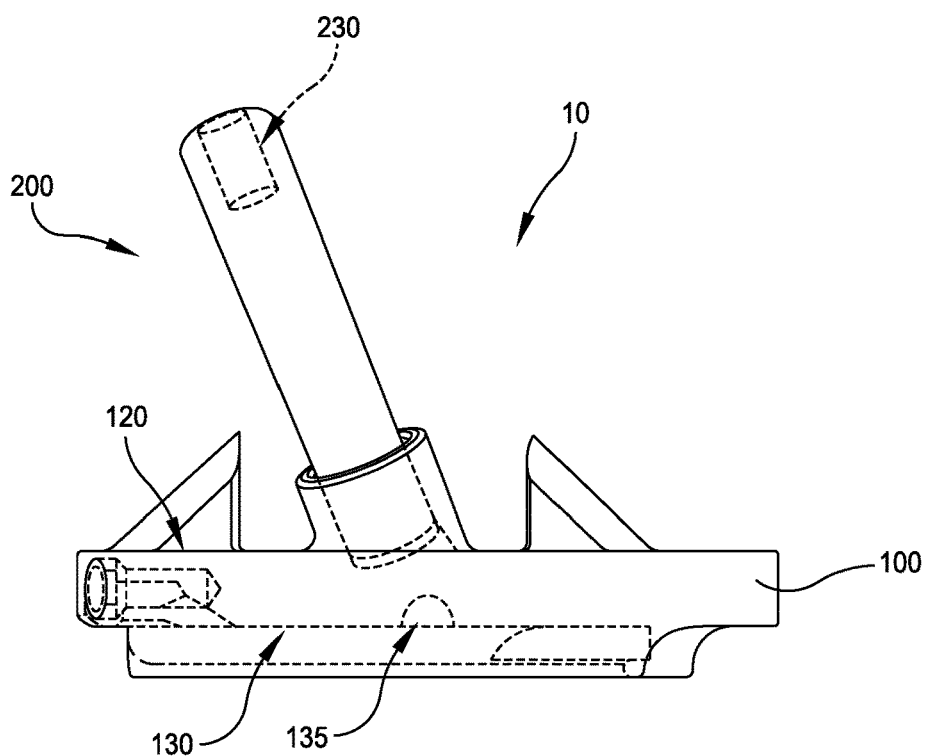

Referring to FIG. 1I, in some embodiments, the connecting portion 220 of the modular stem 200 can be configured with a male-type screw thread and each of the stem connectors 160 is configured as a recess or a blind hole 162 having a corresponding female-type screw thread that forms a threaded connection with the connecting portion 220.

In some embodiments, the shaft portion 210 can be fully or partially configured with a male-type screw thread. The male-type screw thread on the shaft portion 210 can be a cortical-style bone screw thread or a cancellous-style bone screw thread. The provision of bone screw threads at the bone/stem interface could enhance the fixation of the implant in the surrounding bone. Bone threads can also allow for applying a compression of the tibia base component to the resected tibia bone.

In some embodiments, each of the stem connectors 160 can be configured as a post with a male-type screw thread, and the connecting portion 220 of each of the one or more modular stems 200 can be configured as a recess having a corresponding female-type screw thread that forms a threaded connection with one of the stem connectors 160.

The male-type screw threads and the female-type screw threads mentioned above would be tapered screw threads where the corresponding structures involved have tapered surfaces. Otherwise, the screw threads can be straight (non-tapered) screw threads.

In some embodiments, each of the one or more modular stems 200 has a longitudinal axis L and each of the one or more stem connectors 160 has a longitudinal axis LL, and when the connection is formed between one of the one or more modular stems 200 and one of the one or more stem connectors 160, the longitudinal axis L of the one modular stem and the longitudinal axis LL of the corresponding stem connector 160 coaxially align. Where the stem connector 160 is configured as a recess structure with an annular wall that extends from the bone-facing surface 120, the cylindrical shape of the annular wall defines the longitudinal axis LL of the stem connector 160.

In some embodiments, the one or more stem connectors 160 are independently oriented so that their respective longitudinal axes LL are oriented at different angles with respect to the bone-facing surface 120.

Referring to FIG. 1G, each of the one or more modular stems 200 can optionally comprise an alignment feature 230 provided at an end of the shaft portion 210 that is away from the connecting portion 220 to assist in aligning a stem seating tool 500 with the stem 200 described in more detail in connection with FIGS. 3A-3D. In some embodiments, the alignment feature 230 can be a dimple, a slot, a raised bump, etc. to facilitate alignment of the seating tool 500. In some embodiments, the alignment feature 230 can be an elongated dimple or a hole and coaxially aligned with the longitudinal axis L of the modular stem 200 as shown in FIG. 1G to help align the seating tool 500.

Referring to FIGS. 1H, 1I, 4B, and 5A, according to another aspect, the base component 100 comprises a lower surface 130 that is opposite the bone-facing surface 120. A second alignment feature 135 can be provided on the lower surface 130 for each of the one or more stem connectors 160. Similar to the alignment feature 230, the second alignment feature 135 can be any feature that can facilitate locating and aligning the seating tool 500. The second alignment feature 135 can be one or more recesses (i.e. dimples), grooves, raised bumps, etc. Preferably, the second alignment feature 135 is coaxially aligned with the longitudinal axis LL of the corresponding stem connector 160 to assist with aligning the longitudinal axis L of the stem 200 to the longitudinal axis LL of the corresponding stem connector 160, using the stem seating tool 500 along the longitudinal axes LL. When the stem 200 and the corresponding stem connector 160 are aligned so that their longitudinal axes L and LL are coaxially aligned, the aligned longitudinal axes L and LL define an assembly axis for the pair of modular stem and the corresponding stem connector.

In some embodiments, the second alignment feature 135 can have a spherical recess conformation which can allow alignment of multiple modular stems 200 that may be colinear or nearly colinear with the centerpoint of the spherical recess such that the seating tool 500 can be located to one position, and aligned to multiple insertion angles for each of the modular stems 200.

Referring to FIGS. 1A-1E, 1H, 1I, and 5B, for example, in some embodiments, the base component 100 can further comprise one or more additional fixation features 140 such as fins, pegs, bosses, bars, etc. protruding from the bone-facing surface 120. In the illustrated example, the additional fixation features 140 are fins. The additional fixation features 140 are configured to engage a bone surface and enhance the stability of interface between the base component 100 and the bone surface when the base component 100 is seated against the bone surface. The bone surface would usually be a prepared surface. For example, in embodiments where the bone-facing surface 120 of the base component 100 is engaging a tibia, the bone surface can be a resected tibia surface.

The example base component 100 shown in FIG. 1A is configured to receive two modular stems 200 and the stems are angled such that when the base component 100 is applied to a resected surface of the distal end of a tibia, the modular stems 200 allow for some proximal stabilization within the metaphysis of the tibia. The angle of the stems 200 determine how much cortical bone would need to be removed when drilling holes in the tibia for the modular stems 200. If the angle of the holes is more vertical, the holes through the cortex become elongated ellipses, thus sacrificing additional bone material. If the angle is shallower, however, that would result in a shorter stem, and therefore less stabilization in the bone.

The angle of the modular stems 200 in the axial (top-down) view also determines where the stem holes should be located in the long bone, such as a tibia. The two stems 200 shown in FIG. 1A are largely angled in the anterior direction, but they can be configured to be angled toward the medial direction, posterior direction, or lateral direction.

In the example where the base component 100 is being applied to the distal end of a tibia, the cross-section of the tibia in the region where the modular stems would enter to reach the tibia base component 100 is roughly triangular with a vertex of the triangle in the anterior direction. Therefore, splaying the two modular stems 200 to the sides (medial and lateral) can avoid the anterior ridge of the tibia cortex.

Referring to FIGS. 1C and 1D, when the modular stems 200 are connected to the respective stem connectors 160, the longitudinal axis L of the stems are coaxial with the longitudinal axis LL of the stem connectors. As the modular stems 200 are to engage the stem connectors 160 from the medial direction, the modular stems 200 will be introduced into the medullary canal of the tibia via holes H drilled into a side of the tibia at an angle as will be discussed below in connection with FIGS. 2G-2I. The angle of the holes H drilled into side of the tibia is best defined with respect to the resected distal surface DS (see FIGS. 2C and 2D) at the distal end of the tibia because the bone-facing surface 120 of the base component 100 will contact the resected distal surface DS and the angular orientation of the stem connectors 160 are defined with respect to the bone-facing surface 120.

The angular orientation, i.e., the tilt angle, of a stem connector 160 is defined by the longitudinal axis LL of the stem connector 160. This tilt angle will be referred to as β. When the modular stem 200 is properly engaged with the stem connector 160, the longitudinal axis L of the modular stem 200 will be coaxial with the longitudinal axis LL of the stem connector 160 and, thus, the tilt angle of the installed tibia modular stem 200 with respect to the bone-facing surface 120 will also be the tilt angle β. In the implanted position, the bone-facing surface 120 of the base component 100 is intended to be in contact with the resected distal surface DS of the tibia. Therefore the angle of the holes H drilled into the side of the tibia for the modular stems 200 would match the tilt angle β with respect to the resected distal surface DS.

Referring to FIGS. 1C and 1D, the angular orientation of the stem connector 160 tilted by the tilt angle β, which will be the same tilt of the modular stem 200 that engages the stem connector 160, can also be described by two angular components, $\beta_{A-P}$ identified in FIG. 1C and $\beta_{M-L}$ identified in FIG. 1D. The angular component $\beta_{A-P}$ is the angle with respect to the bone-facing surface 120 in the anterior-posterior direction and will be referred to herein as the A-P angle $\beta_{A-P}$. The angular component $\beta_{M-L}$ is the angle with respect to the bone-facing surface 120 in the medial-lateral direction and will be referred to herein as the M-L angle $\beta_{M-L}$.

Referring to FIGS. 2A-2F, before the base component 100 can be implanted into the tibia, the distal end of the tibia is resected with the help of an appropriate guide instrument to prepare a joint space 50. Then, a reamer 60 can be used to form appropriately located recesses R in the resected distal surface DS of the tibia in the joint space 50 to accommodate the stem connectors 160 that protrude from the bone-facing surface 120 of the base component 100.

Figure 2A:
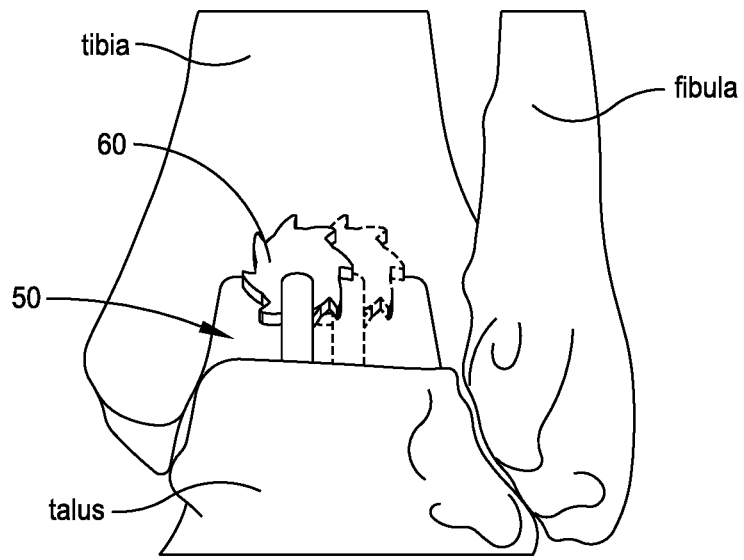
FIGS. 2A-2I are illustrations showing example of a process for preparing an ankle joint space and installing a base according to the present disclosure.
Figure 2B:
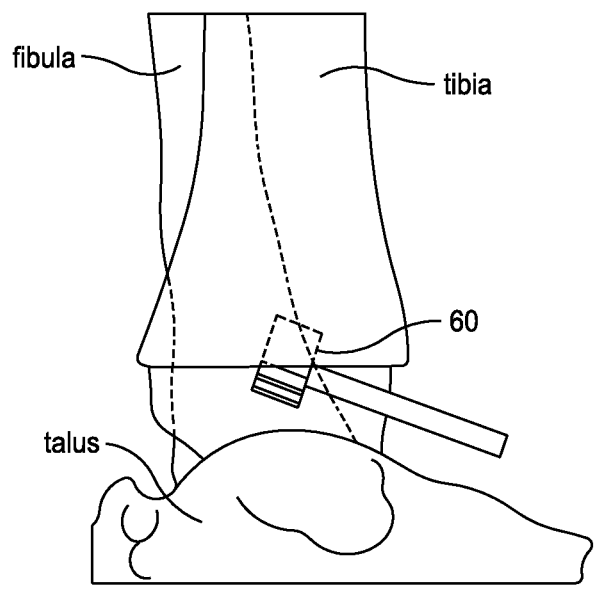
Figure 2C:
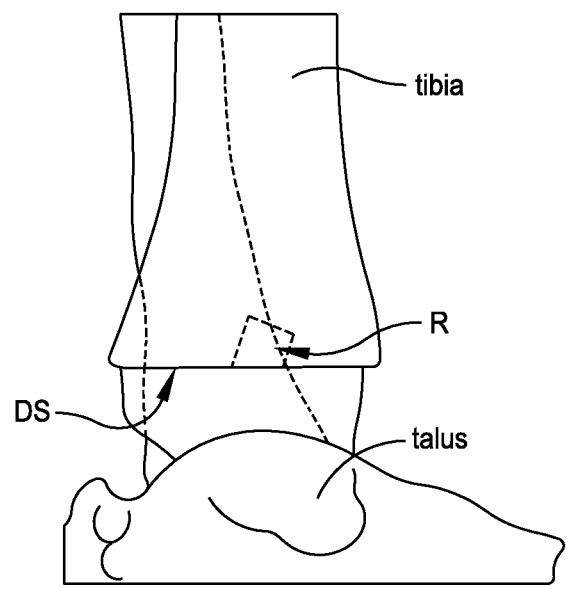
Figure 2D:
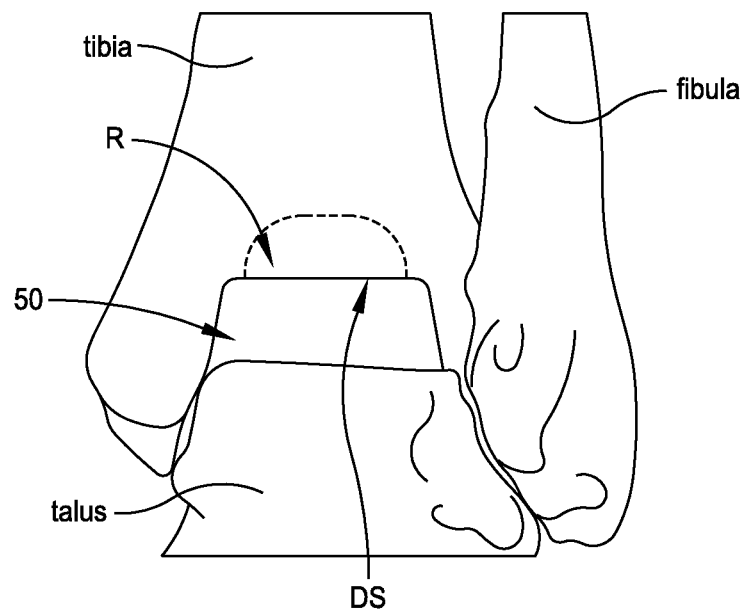
Figure 2E:
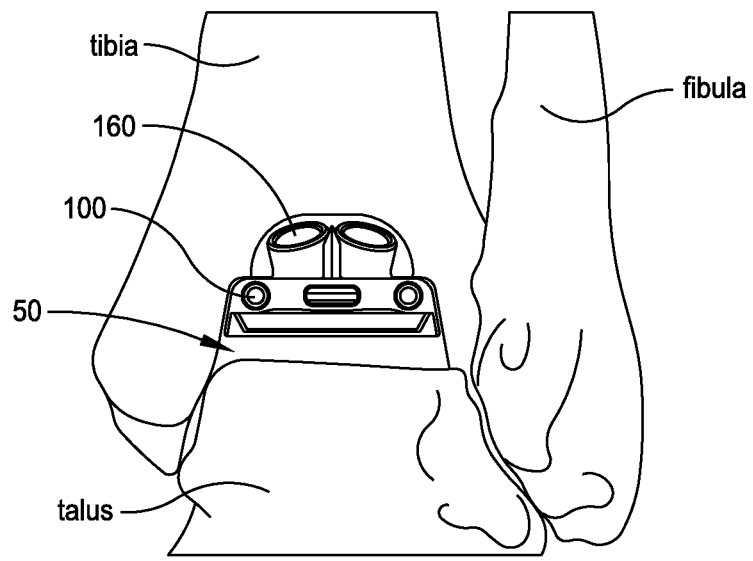
Figure 2F:
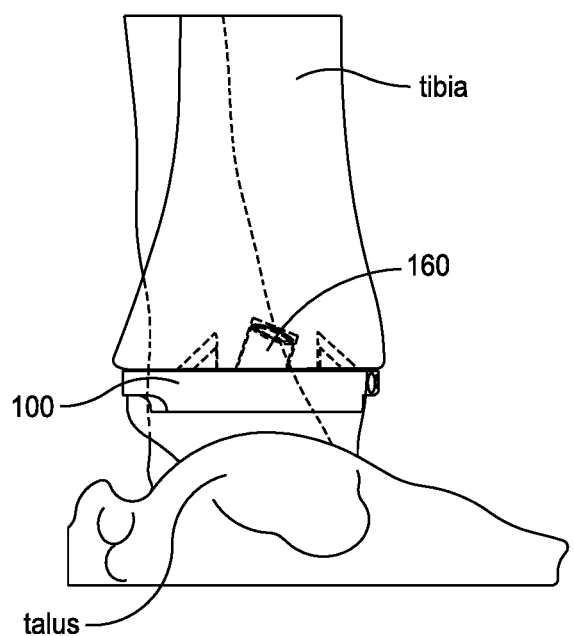
Figure 2G:
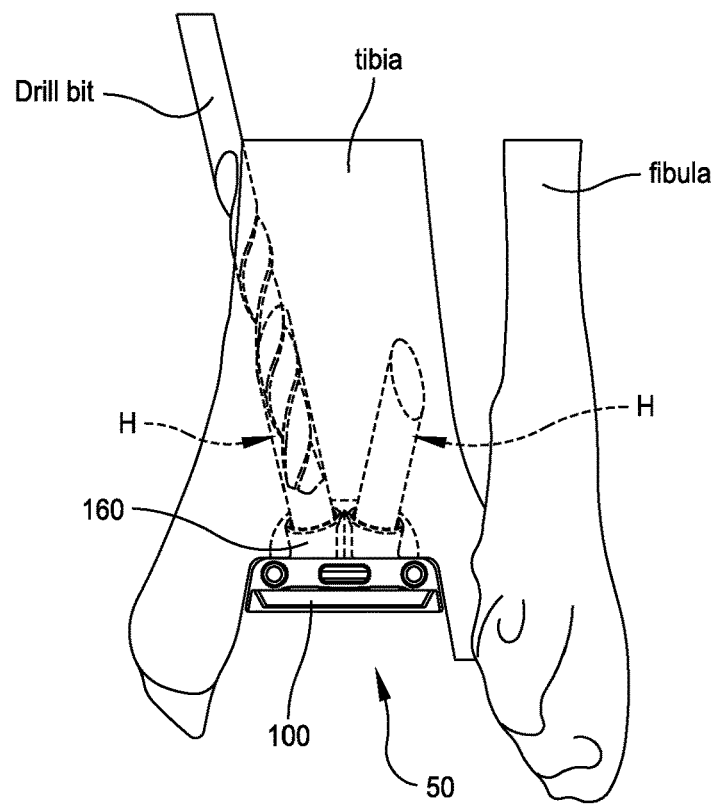
Figure 2H:
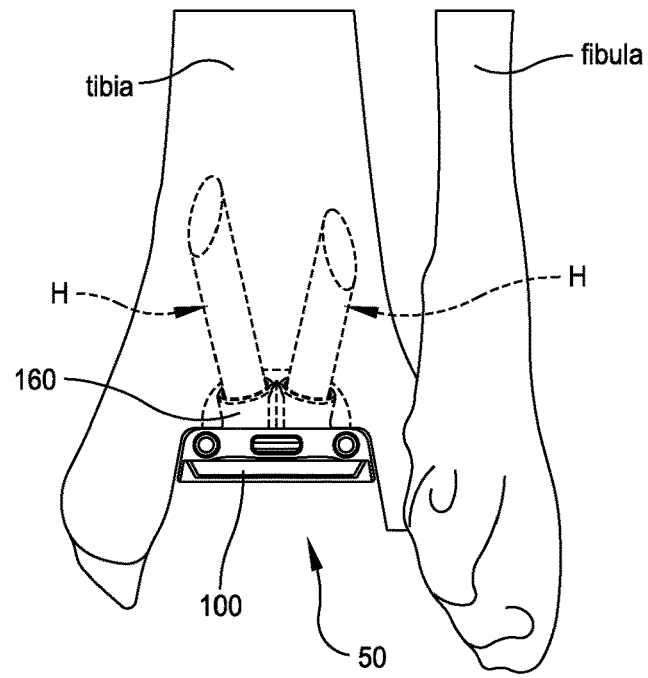
Figure 2I:
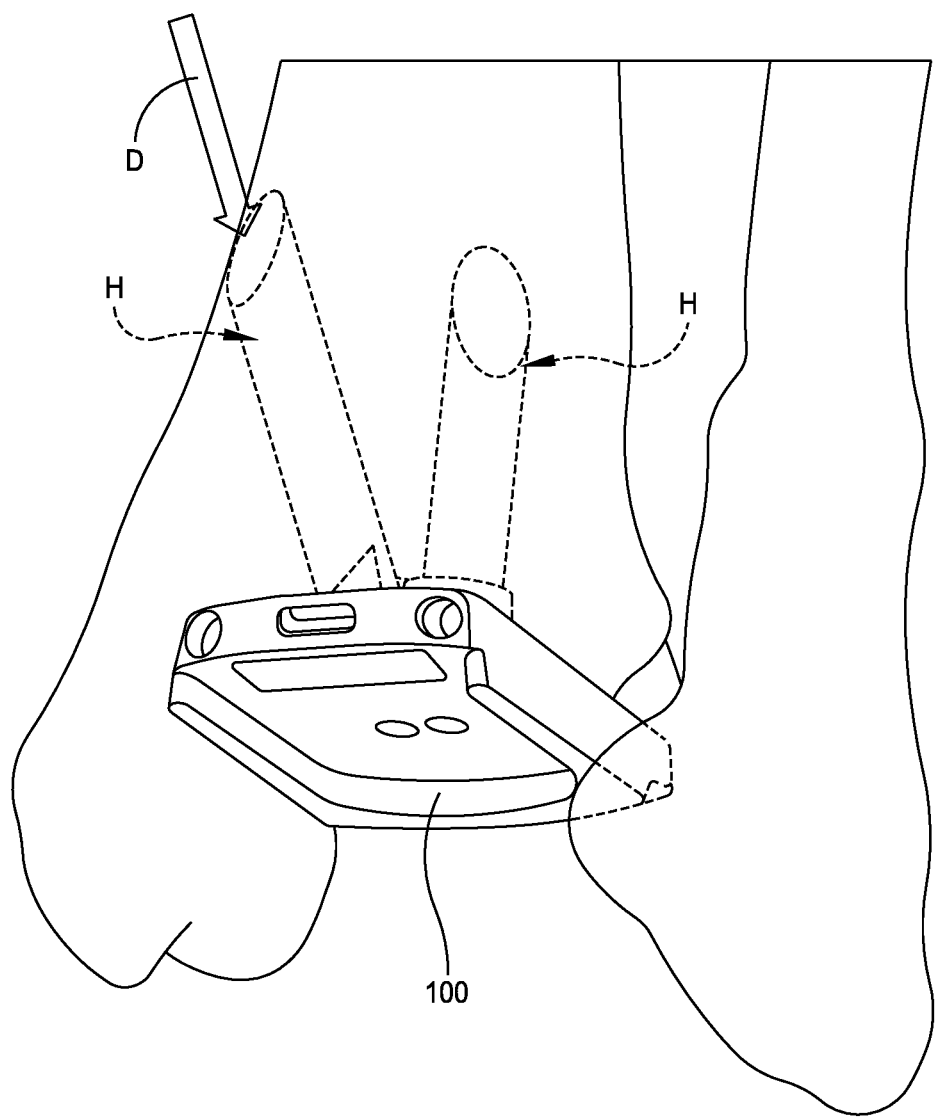

Next, referring to FIGS. 2G-2I, holes H are drilled into the tibia from the proximal side for inserting the modular stems 200. Each hole H is oriented so that the hole is coaxial with the longitudinal axis LL of the corresponding stem connector 160. The drill bit may be aligned using an external fixture and guide system which also sets the tibial resection cuts in the joint space 50 for fitting the base component 100. In an alternative embodiment, the drill bit may be aligned with patient bone scan registration, robotic arms, and/or computer process assisted surgery with visual guidance. Depending on the needs of the patient, the surgeon would determine the number, length, and orientation of the modular stems 200 that would be required to appropriately secure the base component 100 to the tibia. The base component 100 can be offered with a variety of configurations to choose from. The variable features being the number of stem connectors, and the orientation of each of the stem connectors 160. The orientation of the stem connectors would be defined by the A-P angle $\beta_{A-P}$ and the M-L angle $\beta_{M-L}$.

After the holes H are drilled into the tibia, a desired modular stem 200 of appropriate length is inserted into the hole H from the proximal direction indicated by the arrow D in FIG. 2I to engage with a stem connector 160 in the base component 100.

For the embodiment where the connecting portion 220 of the modular stems 200 and the blind hole 162 of the stem connectors 160 have complementary Morse tapered surfaces, the modular stem 200 can be tapped into the stem connector 160 using a punch as one does with a carpentry nail.

In some preferred embodiments, however, the engagement of the modular stem 200 to the stem connector 160 can be achieved using a stem seating tool 500 shown in FIGS. 3A-3D. The seating tool 500 is similar to a channel lock style plier. The seating tool 500 comprises two handles 510a, 510b for actuating the tool pivotally connected by a pivot joint 520, and a clamping end 530 that clamps an assembly of a modular stem 200 and a base component 100 to press the two components together to form the friction lock connection. The clamping end 530 is formed by a pair of jaws, a first jaw 531a, and a second jaw 531b that are configured to oppose each other so that they can capture a modular stem 200/stem connector 160 assembly between the pair of jaws and axially compress the modular stem 200 and the stem connector 160 together in line with the assembly axis (i.e., the longitudinal axes L and LL in alignment) to form the friction lock connection. As mentioned above, the alignment feature 230 that can be provided on the modular stem 200 and the second alignment feature 135 that can be provided on the lower surface 130 of the base component 100 facilitate alignment of the seating tool 500 with the modular stem 200.

Figure 3A:
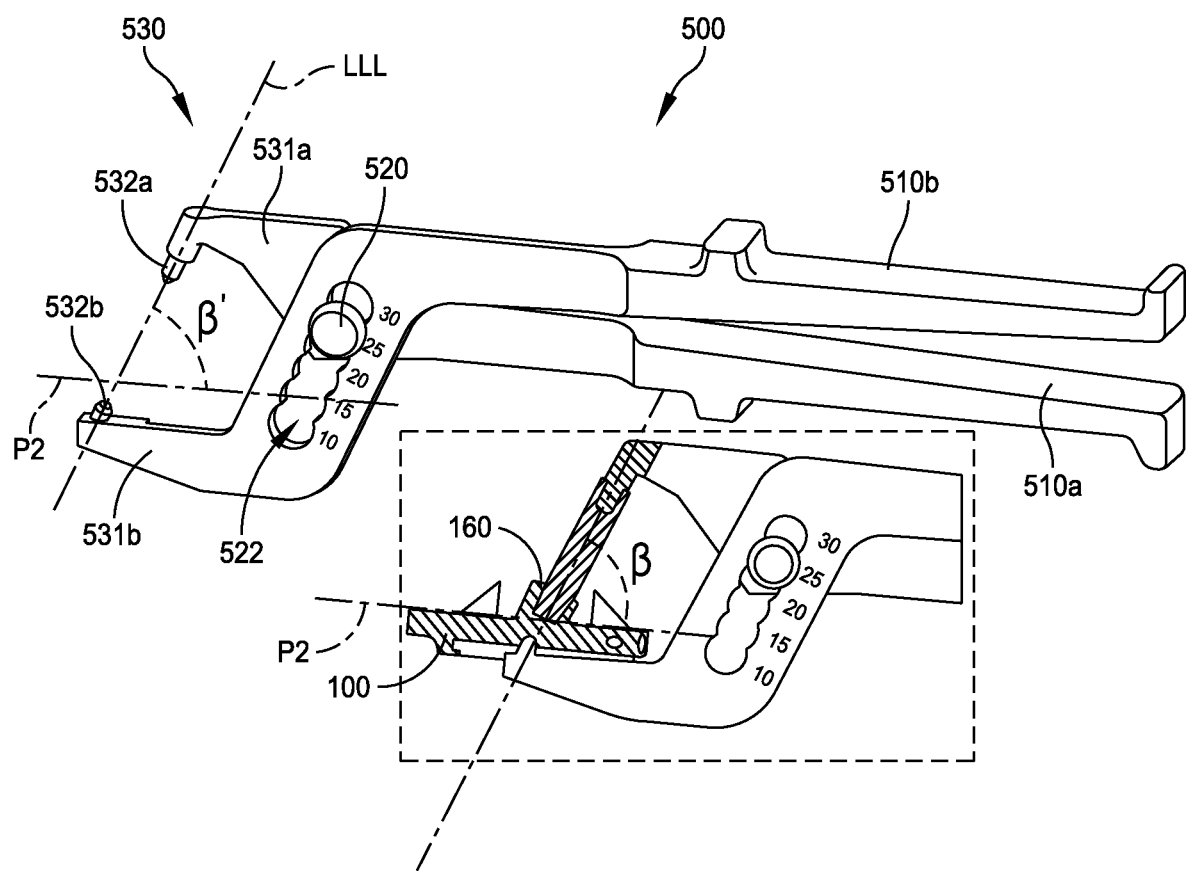
FIGS. 3A-3D are illustrations of a stem seating tool that can be used to securely engage a modular stem to a base according to the present disclosure.

As shown in FIGS. 3A (inset), 3B, and 3D, the pair of jaws 531a, 531b are configured to clamp the modular stem 200/stem connector 160 assembly from the two ends of the assembly and axially compress them until the connecting end 220 of the modular stem 200 and the blind hole 162 are properly engaged to form a friction lock connection. The first jaw 531a is provided with a bump or a protrusion 532a that is sized to fit into the alignment feature 230 of the modular stem 200. The second jaw 531b is provided with a bump or a protrusion 532b that is sized to fit into the second alignment feature 135 on the lower surface 130 of the base component 100. The protrusions 532a and 532b can be simply spherical bumps or they can be elongated protrusions. In embodiments where the protrusions 532a and 532b are elongated protrusions, their extensions are oriented along an axis LLL so that they are axially aligned along the axis LLL as shown in FIG. 3A. That alignment facilitates axially clamping the modular stem 200/stem connector 160 assembly.

Figure 3B:
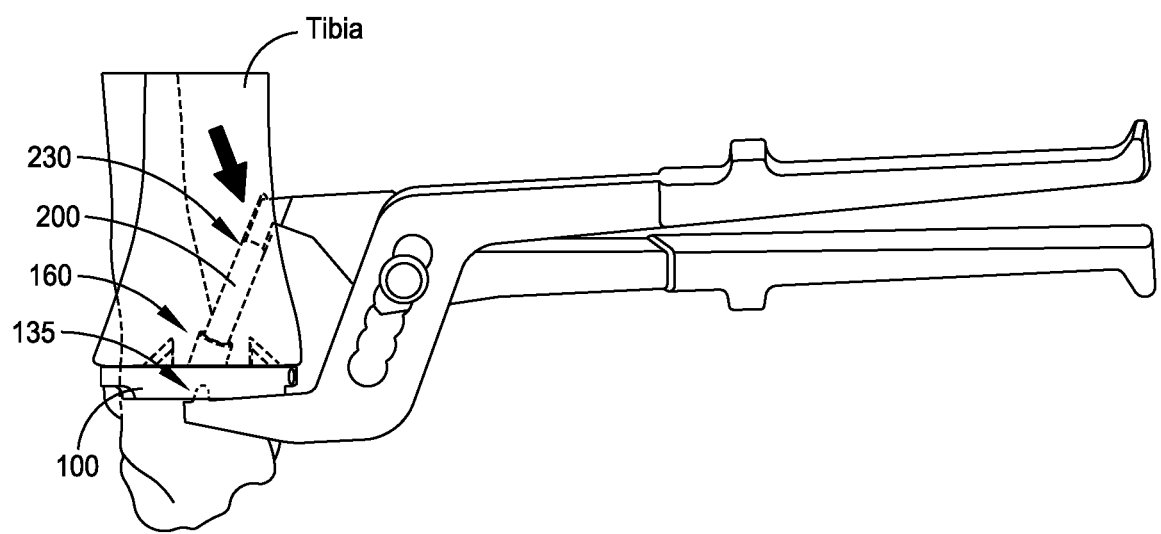
Figure 3C:
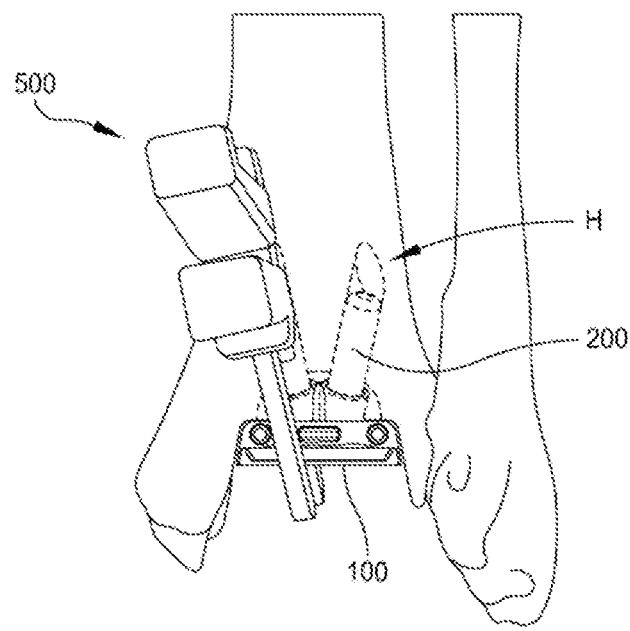
Figure 3D:
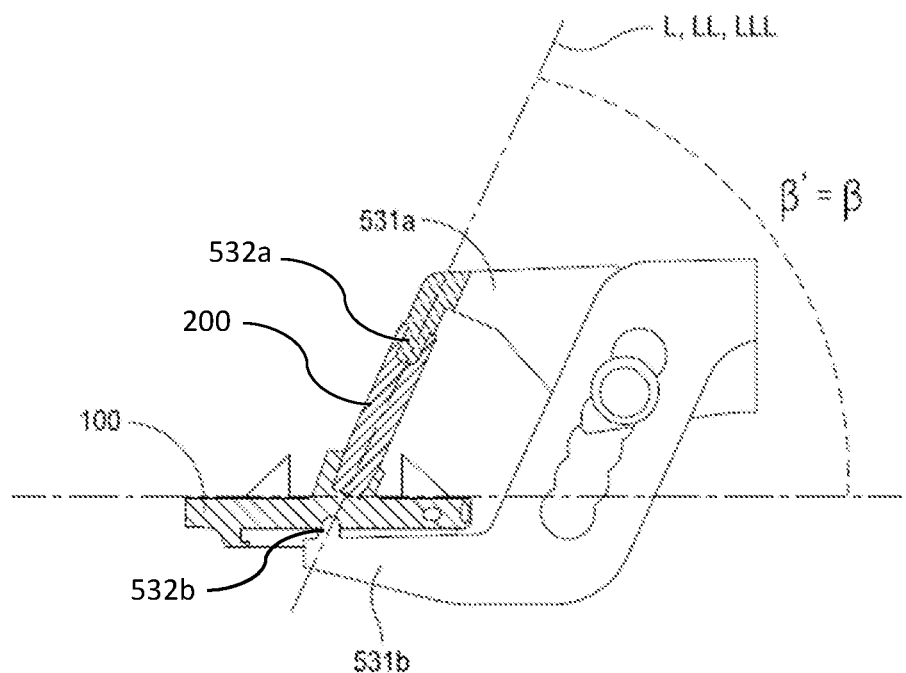

Because the tool 500 needs to engage the base 100 that is situated within the joint space 50 and the modular stem 200 that is inside a hole H in the tibia, the two opposing protrusions 532a, 532b are oriented so that the axis LLL defining their alignment is at an angle β' with respect to the plane P2 that represents the plate of the bone-facing surface 120 of the base component 100. Preferably, the angle β' matches the tilt angle β of the modular stem 200 as it engages the stem connector 160. As described above in connection with FIGS. 1C and 1D, the tilt angle β is defined by the longitudinal axis LL of the stem connector 160. This relationship is illustrated in FIG. 3A and FIG. 3D. It should be noted that the working end of the jaw 531a having the protrusion 532a is shown partially sectioned along with the modular stem 200.

The lengths of the protrusions 532a, 532b can be provided to be any desired length. Particularly, the protrusion 532a provided on the first jaw 531*a*, which is intended to engage the alignment feature 230 on a modular stem 200 after the modular stem 200 is inserted into the hole H in the long bone, is configured to have a length long enough to reach the end of the modular stem 200 that may be at some depth into the hole H. In some embodiments, the tip portion of the first jaw 531*a* where the protrusion 532*a* is provided can be made to be modular so that a tip portion having a desired length protrusion 532*a* can be selected from a variety of sizes.

In some embodiments, the end of the shaft portion of the modular stem 200 may not be equipped with any recessed alignment feature 230. The end of the modular stem 200 can be a stub and the tip of the first jaw 531*a* can be configured with a concave cap-like structure that engages the stub end of the modular stem 200 to exert a compression force.

In some embodiments, the friction lock connection forming structures of the modular stem 200 and the base 100 can be reversed. In other words, the male-type tapered component can be provided on the base 100 and the connecting portion 220 of the modular stem 200 can be provided with a corresponding female-type tapered structure.

In some embodiments, the surface of the modular stems 200 can be prepared as rough, porous for promoting bone on-growth, splined, threaded or smooth. In the illustrated examples, t shaft portion 210 of the stems 200 are cylindrical, but in some embodiments, they can be configured to have non-circular cross-section to achieve selective press-fit.

In some embodiments, the stems 200 can be structured more like fins rather than cylinders to spare more bone in the long bone.

In some embodiments, the stems 200 can have a crucifix cross-section. In some embodiments, the stems 200 can be non-symmetric about the drill axis, such as square, or triangular/prismatic. In some embodiments, the stems 200 can be hollow with perforations in the cortex to allow for injecting bone cement or bone graft substitute material outward from the core of the stem.

In some embodiments, the stems can be shorter than the length of the holes H drilled into the long bone so that the proximal end of the stems 200 are recessed from the exterior cortex surface of the long bone when installed into the base component 100. In other embodiments, the stems can be selected to have a length so that their proximal ends are flush with the exterior cortex surface of the long bone. Pegs interacting with the cortex could provide greater robustness to the stability. In other embodiments, the proximal ends of the stems can be proud of the exterior cortex surface of the long bone. In some embodiments, the proud portion of the stem can have a washer or a head feature. The head feature can be a threaded screw head so that they can provide compression to the distally located base component 100. If the pegs were flush or proud of the cortical bone, this could also facilitate later revision, removal, etc.

Accordingly, a method for implanting the base component 100 for a joint replacement prosthesis onto an end of a long bone can comprise: preparing the end of the long bone in a joint to receive the base component 100; drilling one or more holes H into the long bone from a side, wherein each hole H is oriented so that the hole H is coaxial with the longitudinal axis LL of one of the one or more stem connectors; inserting a modular stem 200 into one of the one or more holes H to engage with one of the one or more stem connectors 160 in the base component 100; and axially compressing the modular stem 200 and the stem connector 160 together to form a connection between the modular stem 200 and the stem connector 160. Preferably, the connection between the modular stem 200 and the stem connector 160 is a friction lock connection.

Figure 1K:
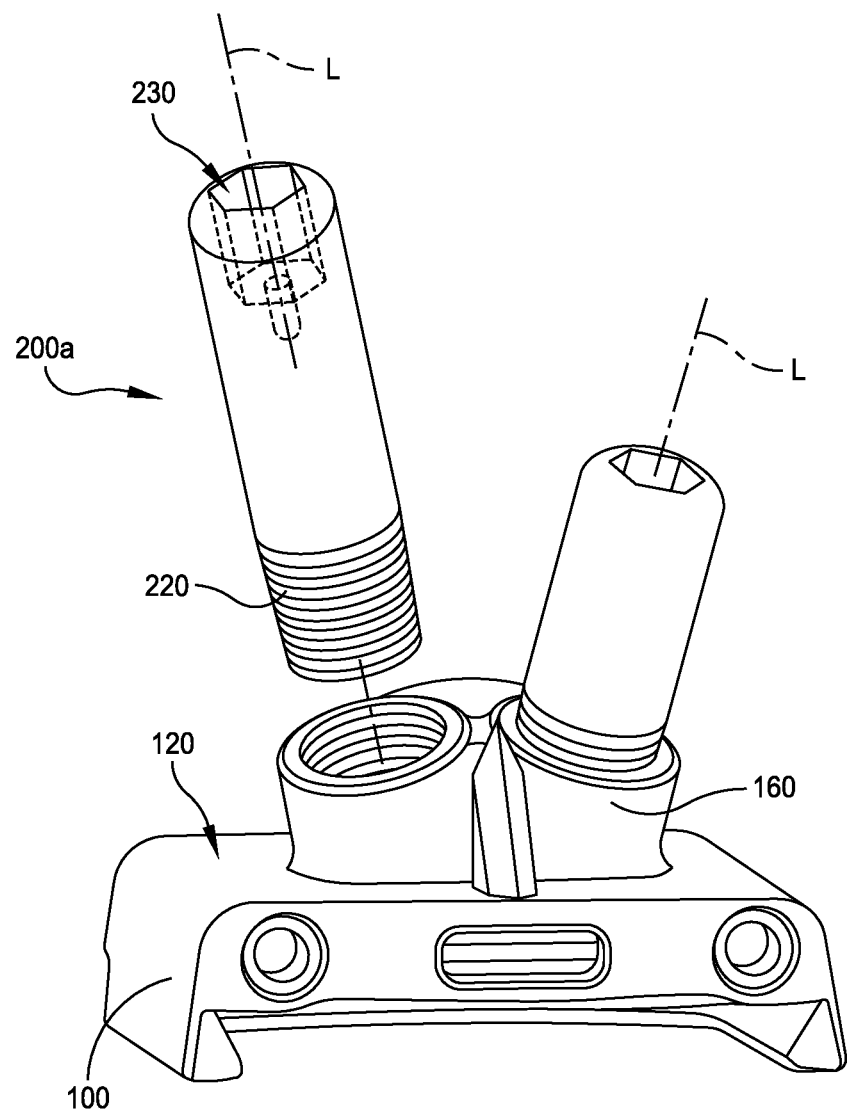
FIG. 1K is an illustration of a base component engaged with two modular stems according to some other embodiments.

Referring to FIG. 1K, for the embodiments where the connecting portion 220 of the modular stem 200*a* and the blind hole 162 of the stem connector 160 are configured with screw threads for threaded engagement. The modular stem 200*a* can be threaded into the stem connector 160. To turn the modular stem 200*a* for threading, the alignment feature 230 provided at the end of the modular stem 200*a* opposite from its connecting portion 220 can be configured to receive a screw driver. In the example shown in FIG. 1K, the alignment feature 230 is configured as a hexagonal shaped recess to receive a male type hex driver but the alignment feature 230 can be configured for any of the known drive mechanism, such as, star-shaped drive, hexalobe drive, philips or crosshead drive, square drive, slotted drive, etc. For accommodating a revision procedure, the threaded connection between the modular stem 200 and the base component 100 might be favored. For this embodiment, after the modular stem 200*a* is inserted into the hole H in the long bone, the screw driver would be inserted into the hole H from the side of the long bone to reach the modular stem 200*a* and turn the modular stem 200*a* for threadedly engaging the corresponding stem connector 160 in the base component 100.

Figure 4A:
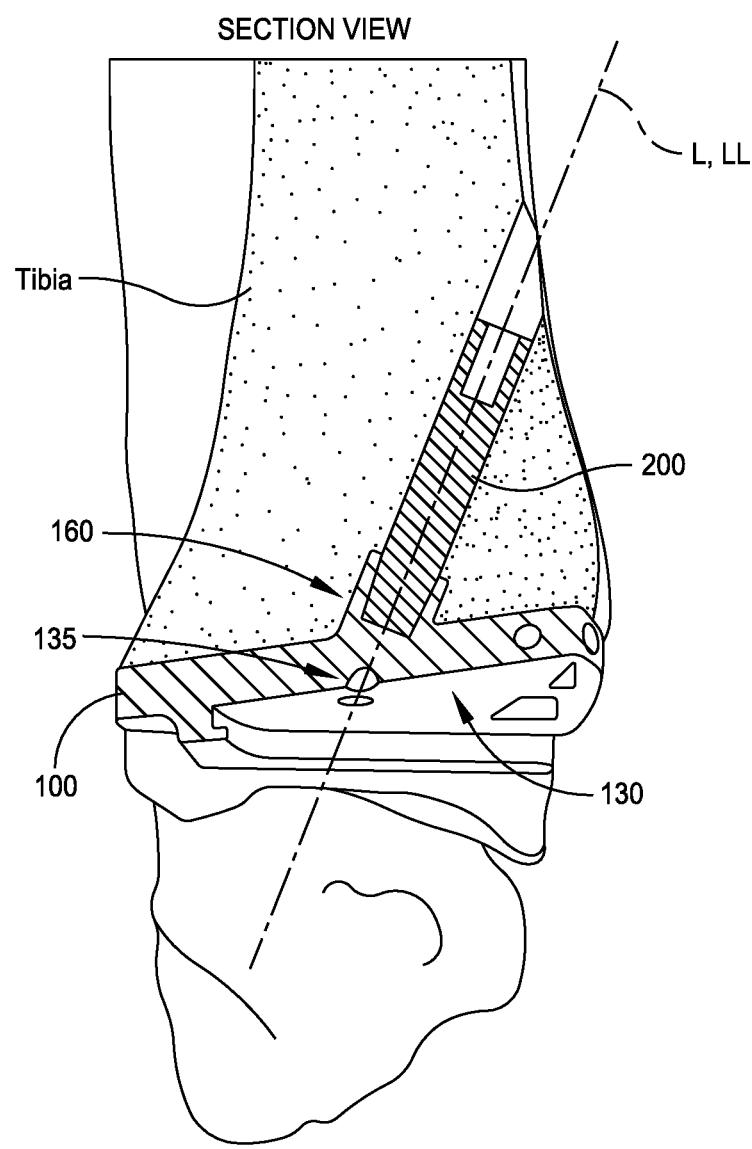
FIG. 4A is a section view of a base/modular stem assembly that has been installed on to a prepared metaphysis region of a distal end of a tibia according to an example application of the joint replacement prosthesis of the present disclosure.
Figure 4B:
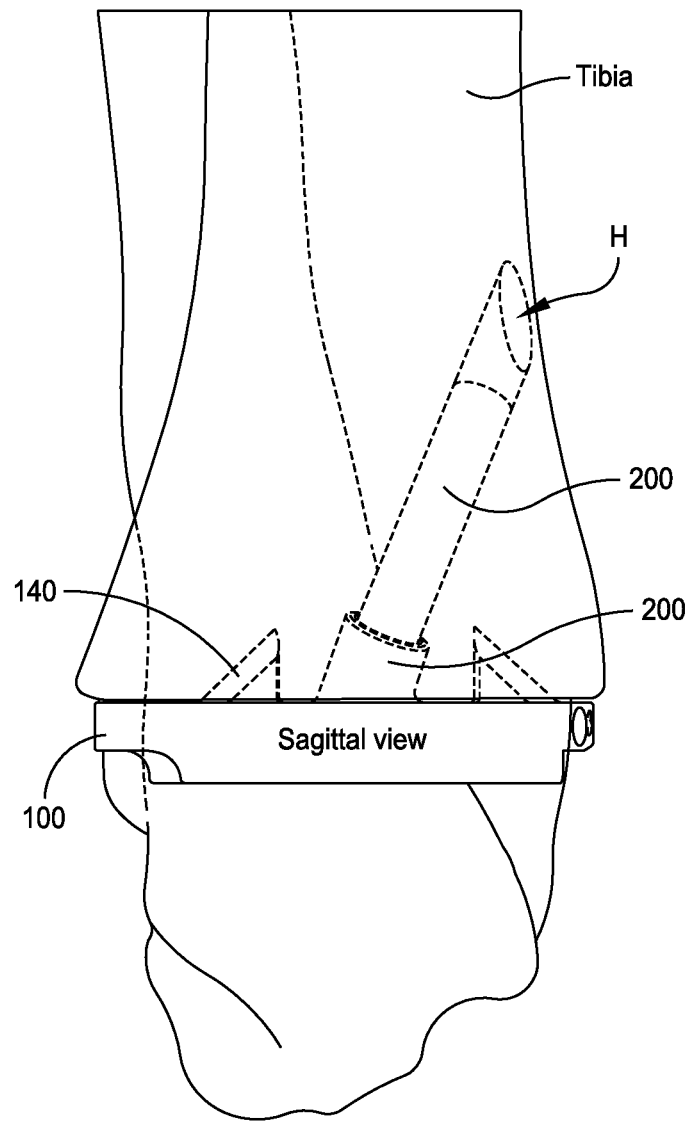
FIGS. 4B-4F are illustrations of various examples of base/modular stem configurations that can be implemented according to the present disclosure.
Figure 4C:
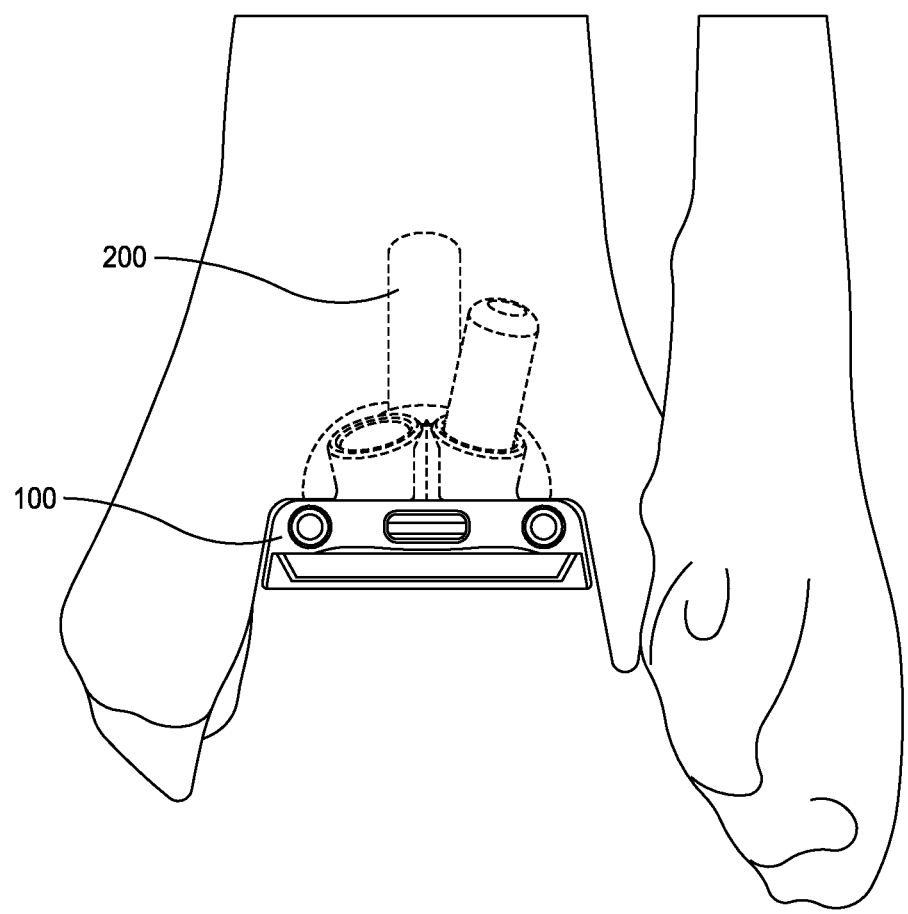

FIG. 4A is an illustration showing a sectioned view of a base component 100 and modular stem 200 assembly in an as-implanted state. The modular stem 200 is engaged with the stem connector 160 of the base component 100. FIGS. 4B-4C are illustrations of various examples of base/modular stem configurations that can be implemented to the distal end of a tibia according to some embodiments.

Figure 4D:
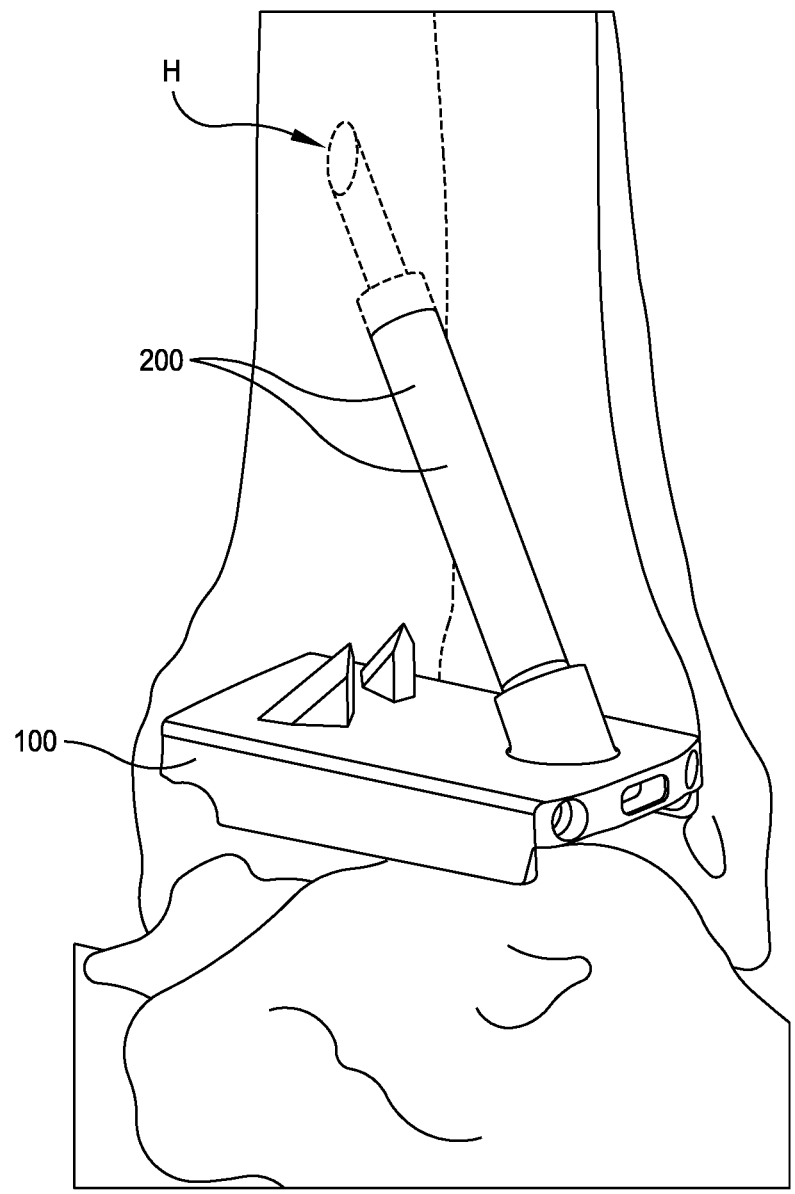
Figure 4E:
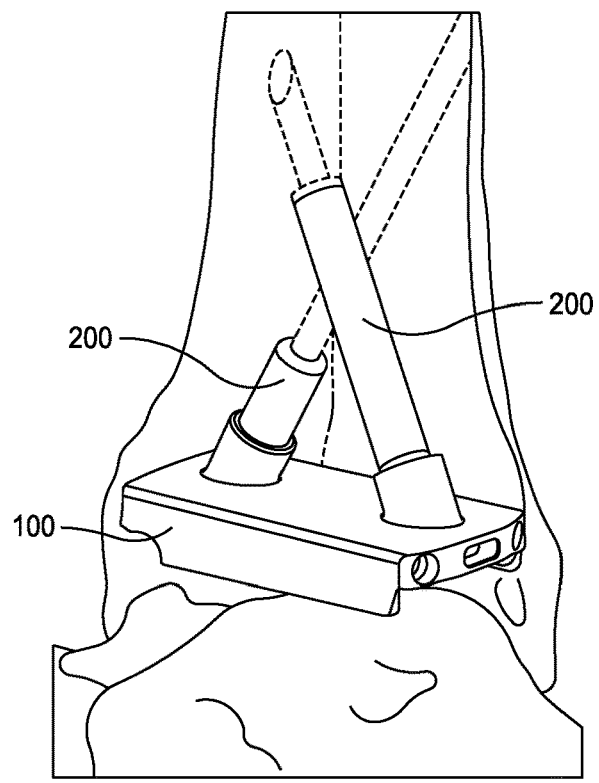
Figure 4F:
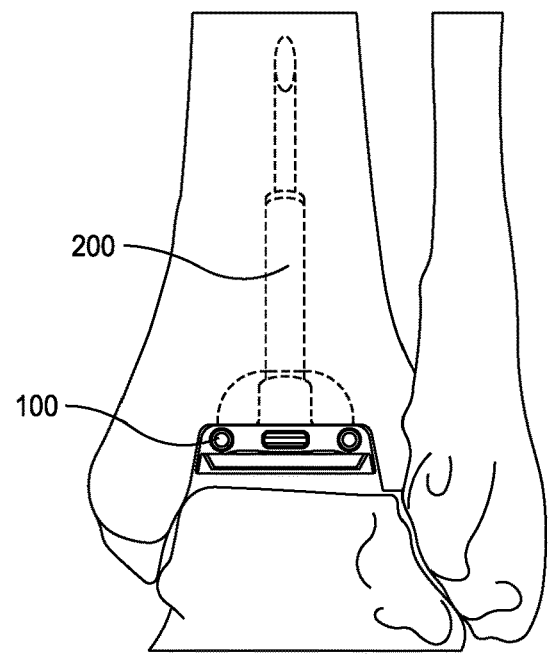

FIGS. 4D-4F are illustrations showing a variation in the configuration of the hole H drilled into a long bone. In the example illustrated here, the hole H does not have a constant diameter throughout its length. Rather, the hole H has two portions each having a different diameter. As shown, the portion of the hole H that receives a stem 200 has one diameter that can accommodate the diameter of the stem 200. The portion of the hole H that exits through the cortical bone along a side of the long bone, however, can have a smaller diameter so that the opening in the cortical bone of the long bone is small. This may be desired depending on the condition of the cortical bone along the side of the long bone or where preserving the cortical bone as much as possible is desired.

In this embodiment, unlike in the embodiment shown in FIG. 2I, because the opening for the hole H in the long bone is too small to insert the stem 200, the stem 200 is inserted from the opposite end of the hole H first, before the base component 100 is brought in position. Then, the stem seating tool 500 can be used in the same manner as shown in FIG. 3B to coaxially compress the stem/base assembly.

In some other embodiments, the structural configurations that enable the modular stems to connect with the base component can be reverse of those of the embodiments described above. For example, referring to FIGS. 5A-5B, in these embodiments, a base component 100A can comprise one or more tapered posts 160A provided on its bone-facing surface 120A, where the tapered posts 160A are configured to receive and form connections with the one or more modular stems 200A introduced from the bone-facing surface side 120A. Correspondingly, each of the one or more modular stems 200A is configured to form the connection with one of the tapered posts 160A. The base component 100A also includes side surfaces 150A and 155A.

In some embodiments, each of the one or more modular stems 200A comprises a shaft portion 210A and a connecting portion 220A and the connecting portion 220A includes a recess 222A that forms the connection with one of the one or more tapered posts 160A by receiving the tapered post therein. In some embodiments, the recess 222A comprises a tapered sidewall surface that forms a friction lock engagement with one of the tapered posts 160A. In some embodiments, the taper on the tapered posts 160A and the taper on the tapered sidewall surface of the recess 222A are Morse tapers.

In some embodiments, the connecting portion 220A on each of the modular stems 200A has a stem connector configured with a female-type screw thread and each of the tapered posts 160A includes a corresponding male-type screw thread.

Similar to the base component 100, in some embodiments, the base component 100A can further comprise one or more additional fixation features 140A such as fins, pegs, bosses, bars, etc. protruding from the bone-facing surface 120A. In some embodiments, the connecting portion 220A has a diameter not greater than the diameter of the shaft portion 210A.

In some embodiments, each of the one or more tapered posts 160A is independently oriented so that their respective longitudinal axes LLA are oriented at different angles with respect to the bone-facing surface 120A.

The seating tool 500 can be used to seat the modular stems 200A onto the tapered posts 160A in the similar manner as used in conjunction with the base component 100 and the modular stems 200 as described herein.

According to some embodiments, the modular stems can be cannulated. For illustration purposes, the cannulation feature 205A is shown in the example modular stem 200A in FIG. 5A but the cannulation is not required to be present along with other features of the modular stem example 200A, such as the recess 222A. In other words, the modular stem example 200 shown in FIG. 1F can be configured with a cannulation. Using such cannulated modular stems can facilitate a surgical technique where a guide pin such as Steinmann pins could be used to assist in establishing the trajectory of the modular stems and confirming the trajectory of the stem paths through the tibia to reach the base component 100, 100A. This can enhance the expectation of the convergence of the modular stems with the intended stem connectors.

The tubular sidewall of such cannulated stem may be perforated. The modular stem 200A in FIG. 5A is shown with perforations 206A along its tubular sidewall. The provision of the perforations 206A allow bone cement or alternative material to be delivered through the cannulation 205A of the stem and out through the perforations 206A into the space around the stem 200A in the patient's bone. This would allow bone cement to fill any gaps between the stem and the surrounding bone, filling voids within the bone. A flowable cement such as PMMA bone cement, or bone graft substitute, either biological or synthetic, or a combination thereof may be used. In some embodiments, a nozzle attachment feature 207A can be provided at the end of the cannulated modular stem 200A to attach a syringe or some other similar cement delivery vessel.

According to some embodiments, the tip of the modular stems 200, 200A on the end opposite from the connecting portion 220, 220A can be shaped to be more accommodating to the geometry of the bone. For example, the end of the modular stem can be configured to have a generous radius (fillet) along the edge to spread the load. An example of this edge 208A is illustrated in FIG. 5A. A more exaggerated broader shape such as a chamfer from one view, with a broad oblique surface matching the shape of the endosteum of the bone at that level could be an option for the design. This would broaden the surface contact between the tip of the modular stem 200, 200A and the endosteum of the bone cortex.

Additionally, when the joint replacement prosthesis of the present disclosure is implanted in the patient, the modular stems 200, 200A do not need to be completely contained within the endosteum space. The stems could be long enough to reach a level where they could interact with the cortical bone, or fill the void left in the cortex that resulted from the drill. The tip of the modular stem could even protrude from the surface of the cortex. The modular stem interacting with the cortex could provide greater robustness to the stability. If the modular stems were protruding from the cortex, this could also facilitate later revision, removal, procedures, etc.

According to another aspect of the present disclosure, in some embodiments of the base component 100, 100A, at least some portions of the surfaces of the base component 100, 100A that come in contact with bone can be coated with a coating that promotes bone in-growth. An example of such coating material is a porous metallic coating ADAPTIS™ by Wright Medical Technology. On the base component 100, the surfaces such as the bone-facing surface 120, 120A, side surfaces 150, 155, 150A, 155A, the outer surfaces of the stem connectors 160, the outer surfaces of the tapered posts 160A, and the surfaces of the fins 140, 140A are examples of the surfaces that can come in contact with bone.

Although the subject matter has been described in terms of exemplary embodiments, it is not limited thereto. Rather, the appended claims should be construed broadly, to include other variants and embodiments, which may be made by those skilled in the art.

What is claimed is:

1. A joint replacement prosthesis comprising:
a base component; and
two or more modular stems;
wherein the base component comprises:
a bone-facing surface including two or more stem connectors, wherein each stem connector is configured to receive and form a connection with one of the two or more modular stems configured to be inserted through a hole in a long bone from the bone-facing surface side, and wherein each of the two or more stem connectors has a longitudinal axis and the stem connectors are independently oriented at different angles with respect to the bone-facing surface so that their respective longitudinal axes are oriented at different angles;
a lower surface that is opposite the bone-facing surface and lower with respect to the bone-facing surface; and
an alignment feature provided on the lower surface for each of the two or more stem connectors, wherein each of the alignment features are coaxially aligned with the longitudinal axis of the two or more stem connectors such that each of the alignment features facilitate alignment of the two or modular stems with the two or more stem connectors.

2. The joint replacement prosthesis of claim 1, wherein each of the two or more modular stems comprises a shaft portion and a connecting portion,
wherein the connecting portion forms the connection with one of the two or more stem connectors, wherein the connecting portion has a diameter not greater than a diameter of the shaft portion.

3. The joint replacement prosthesis of claim 2, wherein the connecting portion is configured with a male-type tapered surface, and each of the stem connectors is configured as a recess having a female-type tapered sidewall surface that forms a friction lock connection with the connecting portion.

4. The joint replacement prosthesis of claim 2, wherein each of the stem connectors is configured as a post with a male-type tapered surface, and the connecting portion of each of the two or more modular stems is configured as a recess having a female-type tapered sidewall surface that forms a friction lock connection with one of the stem connectors.

5. The joint replacement prosthesis of claim 3, wherein the male-type taper on the connecting portion and the female-type taper on the tapered sidewall surface of the stem connector are Morse tapers.

6. The joint replacement prosthesis of claim 4, wherein the male-type taper on the stem connectors and the female-type taper on the tapered sidewall surface of the modular stems are Morse tapers.

7. The joint replacement prosthesis of claim 2, wherein the connecting portion is configured with a male-type screw thread, and each of the stem connectors is configured as a recess having a corresponding female-type screw thread that forms a threaded connection with the connecting portion.

8. The joint replacement prosthesis of claim 7, wherein the shaft portion is fully or partially configured with a male-type screw thread, wherein the male-type screw thread on the shaft portion can be a cortical-style bone screw thread or a cancellous-style bone screw thread.

9. The joint replacement prosthesis of claim 2, wherein each of the stem connectors are configured as a post with a male-type screw thread, and the connecting portion of each of the two or more modular stems is configured as a recess having a corresponding female-type screw thread that forms a threaded connection with one of the stem connectors.

10. The joint replacement prosthesis of claim 7, wherein the male-type screw thread on the connecting portion and the female-type screw thread of the stem connectors are tapered screw threads.

11. The joint replacement prosthesis of claim 9, wherein the male-type screw thread on the stem connectors and the female-type screw thread on the modular stems are tapered screw threads.

12. The joint replacement prosthesis of claim 2, wherein each of the two or more modular stems has a longitudinal axis and when the connection is formed between one of the two or more modular stems and one of the two or more stem connectors, the longitudinal axis of the one modular stem and the longitudinal axis of the one stem connector coaxially align.

13. The joint replacement prosthesis of claim 7, wherein each of the two or more modular stems comprises a second alignment feature provided at an end of the shaft portion that is away from the connecting portion, and the second alignment feature is coaxially aligned with a longitudinal axis of the modular stem.

14. The joint replacement prosthesis of claim 3, wherein the female-type tapered sidewall surface is configured with one or more holes and the male-type tapered surface is configured with a ramp that is aligned with each of the one or more holes when the friction lock connection is formed, wherein the ramp comprises a slanted surface that is oriented such that when a wedge is driven into each of the one or more holes, the wedge operates on the slanted surface of the ramp to disconnect the friction lock connection.

15. The joint replacement prosthesis of claim 4, wherein the female-type tapered sidewall surface is configured with one or more holes and the male-type tapered surface is configured with a ramp that is aligned with each of the one or more holes when the friction lock connection is formed, wherein the ramp comprises a slanted surface that is oriented such that when a wedge is driven into each of the one or more holes, the wedge operates on the slanted surface of the ramp to disconnect the friction lock connection.

16. The joint replacement prosthesis of claim 1, wherein the base component further comprises:
one or more fixation features protruding from the bone-facing surface configured to engage a bone surface and enhance the stability of interface between the base component and the bone surface when the base component is seated against the bone surface.

17. The joint replacement prosthesis of claim 1, wherein the base component comprises one or more surface portions coated with a coating that promotes bone in-growth.

18. A base component for a joint replacement prosthesis comprising:
a bone-facing surface comprising two or more stem connectors, wherein each stem connector is configured to receive and form a connection with one of two or more modular stems configured to be inserted through a hole in a long bone from the bone-facing surface side, and wherein each of the two or more stem connectors has a longitudinal axis and the stem connectors are independently oriented at different angles with respect to the bone-facing surface so that their respective longitudinal axes are oriented at different angles;
a lower surface that is opposite the bone-facing surface and lower with respect to the bone-facing surface; and
an alignment feature provided on the lower surface for each of the two or more stem connectors, wherein each of the alignment features are coaxially aligned with the longitudinal axis of the two or more stem connectors such that each of the alignment features facilitate alignment of the two or modular stems with the two or more stem connectors.

* * * * *